(12) United States Patent
Smith et al.

(10) Patent No.: US 9,314,559 B2
(45) Date of Patent: Apr. 19, 2016

(54) FOUR CHAMBER REDUNDANT-IMPELLER ARTIFICIAL HEART

(71) Applicants: Steve Smith, Trabuco Canyon, CA (US); Peter DeSilva, Rancho Santa Margarita, CA (US)

(72) Inventors: Steve Smith, Trabuco Canyon, CA (US); Peter DeSilva, Rancho Santa Margarita, CA (US)

(*) Notice: Subject to any disclaimer, the term of this patent is extended or adjusted under 35 U.S.C. 154(b) by 0 days.

(21) Appl. No.: 14/095,361

(22) Filed: Dec. 3, 2013

(65) Prior Publication Data

US 2015/0066142 A1      Mar. 5, 2015

Related U.S. Application Data

(60) Provisional application No. 61/872,495, filed on Aug. 30, 2013.

(51) Int. Cl.
*A61M 1/10* (2006.01)
*A61M 1/12* (2006.01)

(52) U.S. Cl.
CPC .............. *A61M 1/101* (2013.01); *A61M 1/1008* (2014.02); *A61M 1/1013* (2014.02); *A61M 1/12* (2013.01); *A61M 2205/17* (2013.01); *A61M 2205/8206* (2013.01); *A61M 2205/8243* (2013.01)

(58) Field of Classification Search
CPC . A61M 1/101; A61M 1/1012; A61M 1/1036; A61M 1/12–1/127; A61M 1/10; A61M 1/1008; A61M 1/1013; A61F 2002/744
See application file for complete search history.

(56) References Cited

U.S. PATENT DOCUMENTS

| | | | | |
|---|---|---|---|---|
| 5,405,383 | A   * | 4/1995  | Barr ............................. | 623/3.15 |
| 7,704,054 | B2  * | 4/2010  | Horvath et al. ................ | 417/213 |
| 2006/0253194 | A1 * | 11/2006 | Dial .............................. | 623/3.13 |
| 2010/0109463 | A1 * | 5/2010  | Jiang et al. ................... | 310/90.5 |
| 2010/0168848 | A1 * | 7/2010  | Horvath et al. .............. | 623/3.13 |
| 2011/0144744 | A1 * | 6/2011  | Wampler ...................... | 623/3.13 |
| 2011/0201870 | A1 * | 8/2011  | Forsell ............................ | 600/16 |

* cited by examiner

*Primary Examiner* — Howie Matthews
(74) *Attorney, Agent, or Firm* — Roy A. Ekstrand

(57) ABSTRACT

An artificial heart for use in a human recipient includes a housing within which a quartet of turbine pump segments are operative. The quartet of turbine pump segments provides a redundancy which in turn enhances the safety factor provided by the artificial heart. A controller is powered by a rechargeable battery and is operative to apply appropriate drive signals to the motor drives of the turbine pump segments. The battery may be implanted along with the controller to avoid the need for any external connections to the artificial heart. An inductively coupled battery charger for use outside the recipient's body is positioned proximate the battery charger to provide inductively coupled charging for use in driving the artificial heart.

12 Claims, 14 Drawing Sheets

FOUR CHAMBER REDUNDANT-IMPELLER ARTIFICIAL HEART

CROSS-REFERENCE TO RELATED APPLICATIONS

This application claims the benefit of and priority under 35 U.S.C. 119(e) of U.S. Provisional Patent Application 61/872, 495, entitled DUAL-STAGE REDUNDANT-IMPELLER ARTIFICIAL HEART, filed Aug. 30, 2013 in the names of Steve Smith and Dr. Peter DeSilva, the disclosure of which is incorporated herein by reference.

FIELD OF THE INVENTION

This invention relates generally to apparatus for sustaining and continuing life for patients having failing or failed hearts and particularly to artificial heart replacement devices used therein.

BACKGROUND OF THE INVENTION

For many years, practitioners in the medical treatment and medical device arts have endeavored to provide artificial heart devices constructed to replace a failed or failing heart within a recipient. The most basic need is the creation of a replacement pumping device which is capable of performing the basic blood pumping and circulation functions of the natural heart.

Early attempts to provide a sustainable heart replacement were severely limited by the available technologies and the state of the art at that time. Devices proved to be generally too large and unwieldy and, for the most part, impractical. With the continuing advances in the related technologies and creative arts, heart replacement devices became smaller, more reliable and, in some instances, at least partially implantable within the recipient. Such "implantable" devices have generally remained hybrid devices in that the actual pump may be implanted within the recipient while additional support apparatus remains external to the patient and remains connected to the implanted device by a plurality of connecting wires and hoses.

Because of the complexity of human body systems and the complications and consequences of heart replacement device failure, the requirements for an implantable artificial heart remain daunting and, for the most part, heretofore largely unattained.

By way of example, a successful artificial heart replacement device must, above all, be long lasting and reliable. The dire consequences to the device recipient brought about by device failure make this requirement all too apparent. In addition, however, the device must be small enough to be implantable within the recipient's chest and efficient enough to maintain adequate blood circulation to sustain normal life functions. The device must avoid undue stress upon the recipient's circulatory and pulmonary systems. The device must also be capable of adjusting to and compensating for different recipient activity levels and stresses. Additional requirements such as avoidance of blood cell damage by the pumping apparatus and the prevention of the blood clot forming stagnation regions make further demands upon the heart replacement device.

While practitioners in the medical treatment and medical device arts have created a virtually endless number of proposed artificial heart replacement devices, there remains nonetheless a continuing unresolved need in the art for an improved, implantable, reliable and effective artificial replacement device which meets the stringent, unforgiving and vital requirements and challenges posed by a truly fully functioning completely implantable heart replacement device.

SUMMARY OF THE INVENTION

Accordingly, it is a general object of the present invention to provide an artificial replacement device which is reliable, implantable and effective. It is a more particular object of the present invention to provide an improved artificial heart replacement device which avoids the need for external component apparatus and which signals events or anomalies within the system while shifting to backup remedial life sustaining operation.

In accordance with the present invention, there is provided an artificial heart comprising: a housing having a first input, a first output, a second input and a second output; a first turbine pump operative to flow blood from said first input to said first output; a second turbine pump operative to flow blood from said second input to said second output; a third turbine pump operative to flow blood from said first input to said first output; and a fourth turbine pump operative to flow blood from said second input to said second output.

The present invention improves the art by providing a four stage redundant impeller artificial heart. Within the housing a pair of electrically-driven impeller drive motors facilitate the pumping of blood from the vena cava (returning from the body) to the pulmonary arteries and thereafter returning to the second pump stage from the pulmonary veins to be further pumped out to the aorta. The use of dual pump drives for the pump turbines is configured to provide pump redundancy should a pump fail. In such case the remaining operative motor/pump drives the turbines coupled thereto with sufficient capability and circulation to maintain life in the recipient until remedial intervention may be preformed. The inputs to the pump and outputs from the pump support sensors coupled to a dual microprocessor drive controller. Each microprocessor drive controller is operatively coupled to both of the redundant pump drive motors. Sensors are also provided to monitor the operation of each pump system. A pair of battery modules each including an inductively coupled charging device are implanted within the patient abdomen and operatively coupled to the processor controller and the drive motors. A pair of inductive battery charging modules are supported upon an abdominal belt and coupled to a source of operative electrical power. Battery charging is accomplished by inductive coupling through the body tissue between the external charging modules and the implanted battery and charger apparatus. The dual redundant micro controller is also implanted within the recipient's body.

From another perspective, the present invention provides an artificial heart comprising: a housing having a first input, a first output, a second input and a second output; a first turbine pump operative to flow blood from the first input to the first output; a second turbine pump operative to flow blood from the second input to the second output; a third turbine pump operative to flow blood from the first input to the first output; and a fourth turbine pump operative to flow blood from the second input to the second output.

In a preferred fabrication of the present invention artificial heart, the first and second turbine pumps as well as the third and fourth turbine pumps are arranged in series pairs within the blood flow. The turbine pumps are supported within a housing defining a pair of straight-through blood flow paths, each supporting one of the series pairs of turbine pumps.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

DESCRIPTION OF THE PREFERRED EMBODIMENT

By way of overview, the present invention artificial heart includes a housing enclosure suitable in size and shape for implanting within a recipient. The housing supports a pair of servomotor drives each of which is operatively coupled to a pair of turbine blades. A pair of fluid manifolds are formed on each end of the housing each enclosing a pair of turbine pump vanes, or blades, and having fluid coupling chambers for receiving an input blood flow and for discharging an output blood flow under the influence of the rotating turbine blades. A pair of input sensors is operatively coupled to each of the blood inputs and a pair of output sensors is operatively coupled to each of the pump outputs. Each of the sensors comprises a pressure responsive transducer and each are operatively coupled to a dual processor drive control. The first of the blood inputs is coupled to the source of returning blood supply from the patient's vena cava. The output of the corresponding pump section is coupled to the pulmonary arteries of the recipient. The remaining pump input is coupled to the pulmonary veins carrying the blood returning from the recipient's lungs. The corresponding pump output stage is coupled out to the recipient's body via the recipient's aorta. The dual controller is cooperative with the plurality of pressure transducer sensors to monitor the performance and function of the artificial heart. Each of the servomotor pump drives is controlled by a respective one of the redundant microprocessor controllers. In the event of a failure within one of the servomotors driving the turbine pumps, the controller maintains sufficient output using the remaining operative servomotor to maintain vital functions in the recipient. The controller is also configured to provide external communication of pump operation and any fault conditions, or other anomalies to an external monitoring facility.

Figure 1:
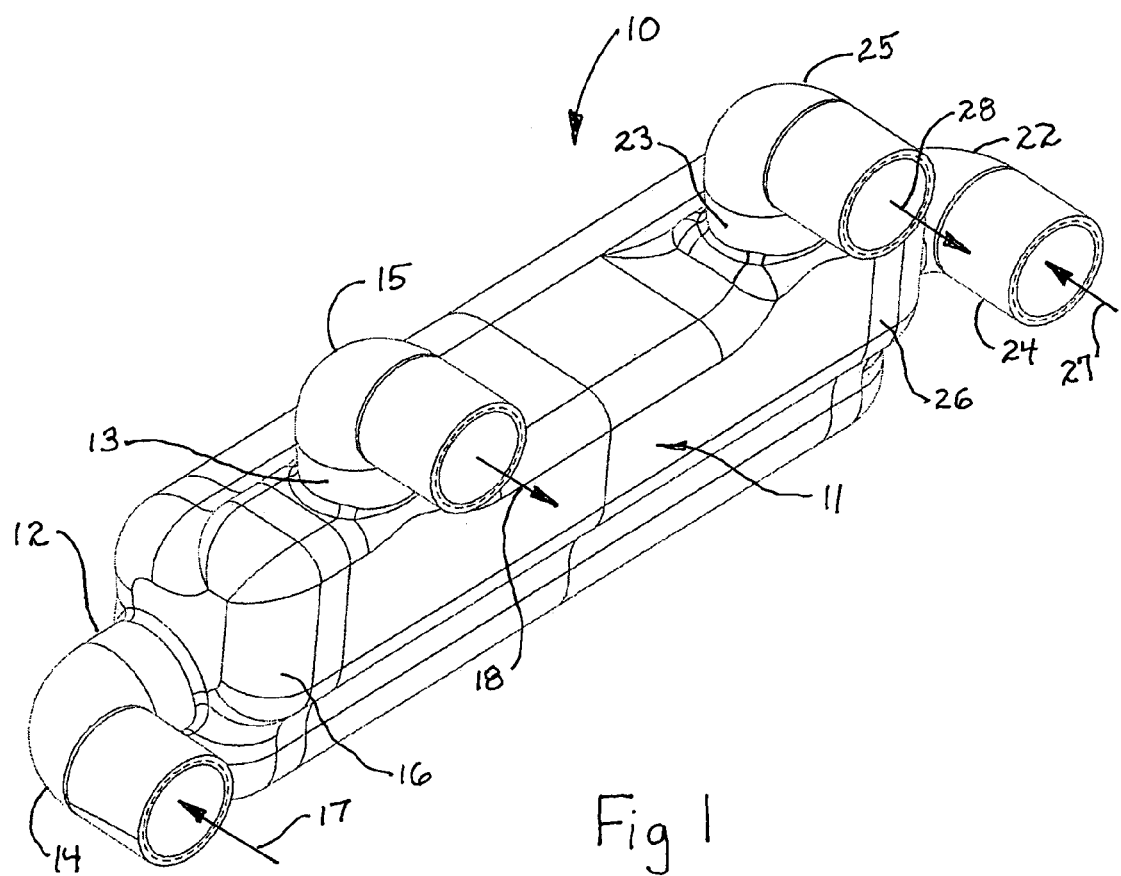
FIG. 1 sets forth a perspective view of the present invention dual-stage redundant-impeller artificial heart.

More specifically, FIG. 1 sets forth a perspective view of a dual-stage redundant-impeller artificial heart constructed in accordance with the present invention and generally referenced by numeral 10. Artificial heart 10 includes an elongated housing 11 supporting a pair of manifolds 16 and 26 at opposite ends thereof. Manifold 16 in turn supports an input coupling 12 to which a right angle coupler 14 is joined. Similarly, manifold 26 supports an input coupling 22 (better seen in FIG. 3) which in turn supports a right angle coupler 24. Housing 11 further supports and output coupling 13 joined to a right angled coupler 15 and an output coupling 23 joined to a right angled coupler 25.

In operation, and by means described below in greater detail, is operatively coupled to the host patient's superior vena cava and inferior vena cava utilizing conventional couplings (not shown). Similarly, coupler 15, joined to output 13, is operatively coupled to the host patient's pulmonary arteries also using conventional coupling apparatus (not shown). Coupler 24 which is joined to input 22 is operatively coupled to the host patient's pulmonary veins by conventional coupling apparatus (not shown). Finally, coupler 25 which is joined to output 23 is operatively coupled to the host patient's aorta by conventional coupling apparatus (not shown).

In operation, and by means set forth below in greater detail, blood returning from circulation through the patient's body is coupled via the patient's superior vena cava and inferior vena cava to coupler 14 and to manifold 16 of pump 10 via input 12. Thus, blood returning from the patient's body is pooled and coupled to manifold 16. Within manifold 16, by means set forth below in FIG. 7, returning blood is pumped through manifold 16 to output 13 and thereafter to coupler 110 to the host patient's pulmonary arteries. Blood is then circulated through the patient's lungs and thereafter is coupled to input 22 via coupler 100. Within manifold 26, a pair of turbine pumps (also seen in FIG. 7) are operative to pump the returning blood outwardly through output 23 and coupler 120 to the host patient's aorta.

Returning to FIG. 1, in the operation of pump 10 set forth below and described in greater detail, blood is pumped/drawn into coupler 14 in the direction indicated by arrow 17 and thereafter pumped outwardly through output 13 and coupler 15 in the direction indicated by arrow 18. Further, blood is returned to coupler 24 and input 22 to flow in the direction indicated by arrow 27 within manifold 26 a pair of pump turbines (seen in FIG. 7) are operative to pump blood outwardly through output 23 and coupler 25 in the direction indicated by arrow 28. In this manner, the circulating function of a normal heart is maintained by the operation of artificial heart 10. The structure of artificial heart 10 is described below in greater detail. However, suffice to note here that the utilization of a pair of redundant servomotor pump drives and pump turbine sets provides a redundancy for the patient which greatly increases overall system reliability. It will be understood by those skilled in the art that housing 11, manifolds 16 and 26, inputs 12 and 22, outputs 13 and 23 and couplers 14, 15, 24 and 25 are all fabricated of a suitable material which may be utilized for implanting within the host patients body. Similarly, it will be apparent to those skilled in the art that couplers 14, 15, 24 and 25 are fabricated to cooperate with and be compatible with conventional couplings presently utilized in connecting an artificial heart to a patients veins and arteries.

Figure 2:
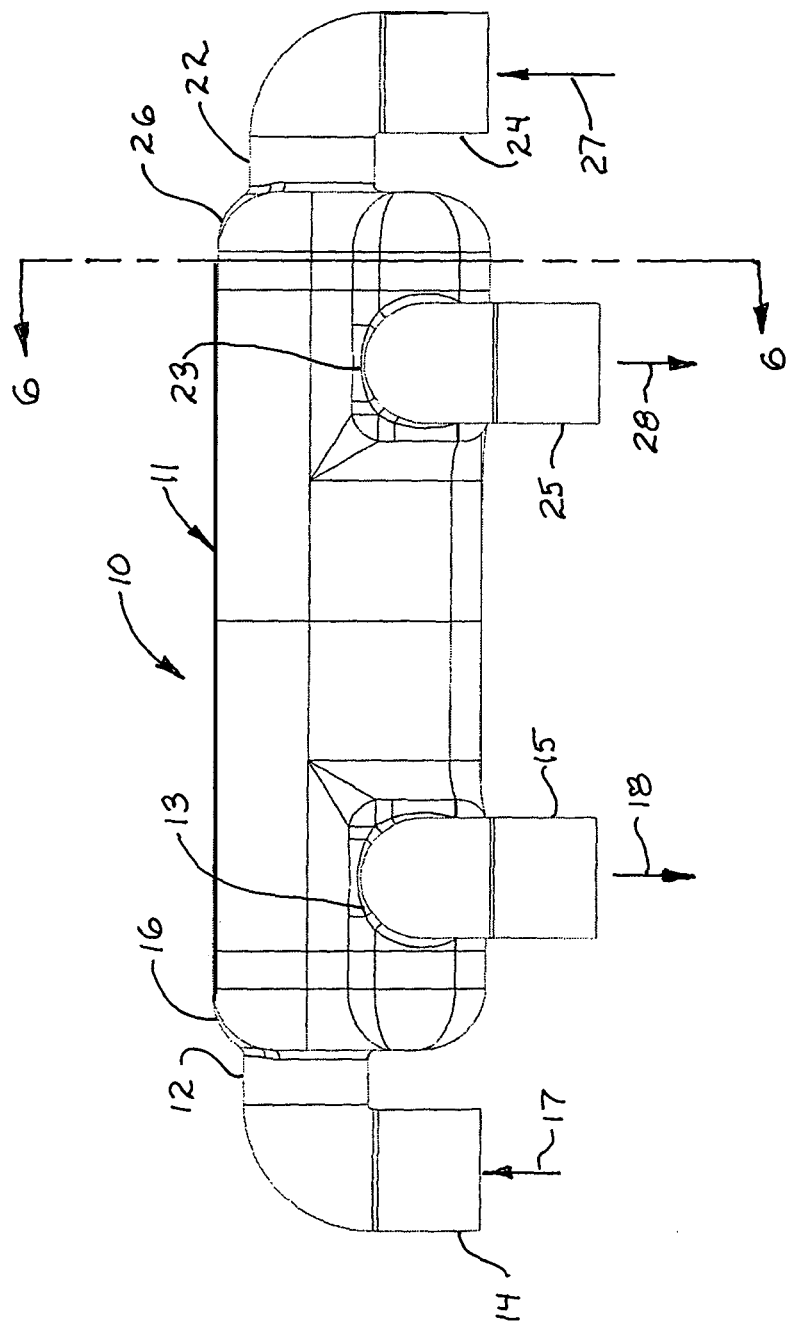
FIG. 2 sets forth a top view of the present invention dual-stage redundant-impeller artificial heart.

FIG. 2 sets forth a top view of artificial heart 10. As described above, artificial heart 10 includes a housing 11 supporting a pair of manifolds 16 and 26 at opposite ends thereof. As is also described above, manifolds 16 and 26 support respective inputs 12 and 22 which in turn are coupled to respective couplers 14 and 24. Housing 11 further supports a pair of outputs 13 and 23 which in turn are joined to and support a pair of couplers 15 and 25. Once again, it will be noted that in the operation of artificial heart 10 blood is initially received within coupler 14 flowing in the direction indicated by arrow 17 and is pumped outwardly from output 13 and coupler 15 in the direction indicated by arrow 18. Further, blood is returned to artificial heart 10 to flow through coupler 14 and input 22. Thereafter, blood is pumped outwardly from artificial heart 10 through output 23 and coupler 25 to be recirculated within the host patient's circulatory system.

Figure 3:
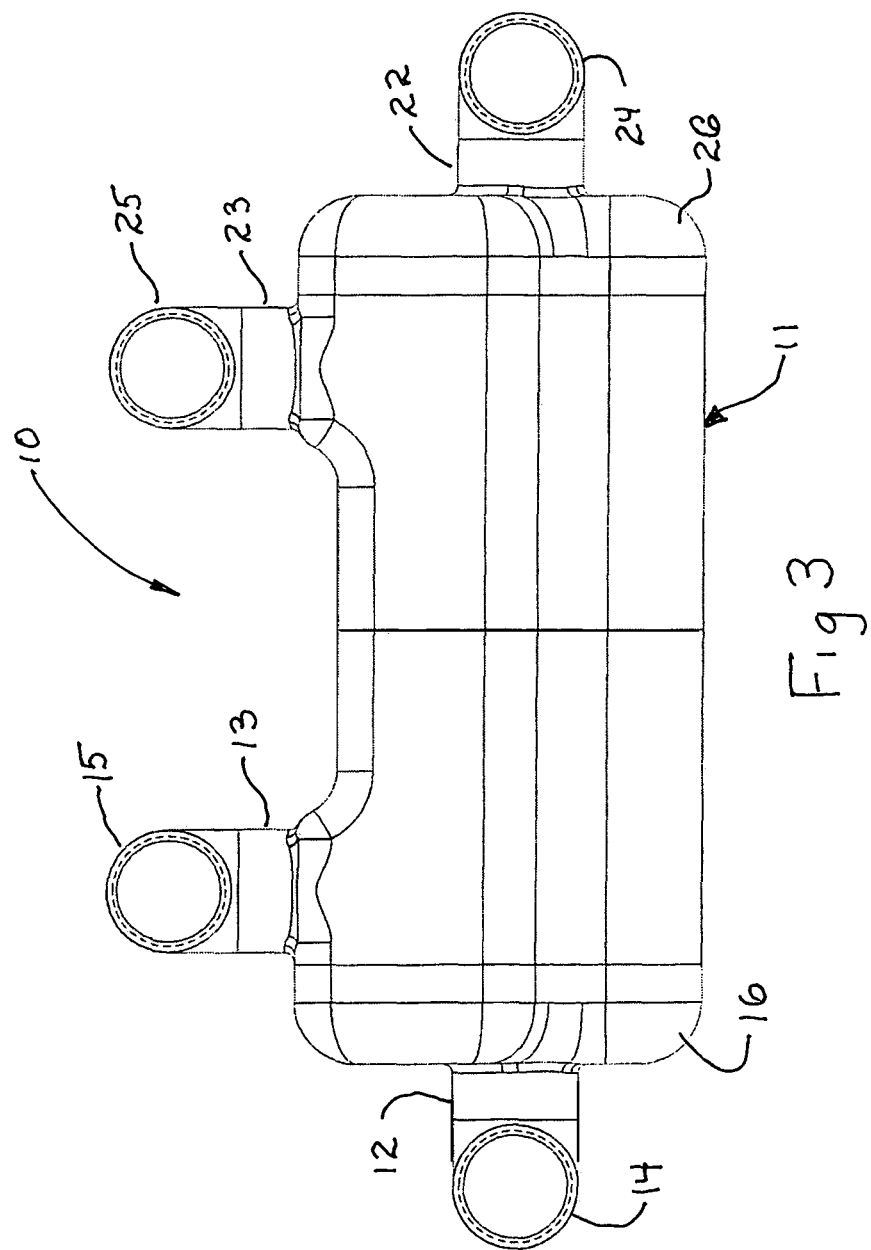
FIG. 3 sets forth a front view of the present invention dual-stage redundant-impeller artificial heart.

FIG. 3 sets forth a front view of artificial heart 10. As described above, artificial heart 10 includes a housing 11 supporting a pair of mirror image manifolds 16 and 26 on opposed ends thereof. As is also described above, manifolds 16 and 26 include respective inputs 12 and 22 which in turn support respective couplers 14 and 24. Housing 11 further supports outputs 13 and 23 which in turn support respective couplers 15 and 25. As described above, artificial heart 10 is preferably formed of a molded material and is generally configured to provide blood flow manifolds 16 and 26 at opposite ends of housing 11 which in turn facilitates blood flow into manifold 16 through coupler 14 and input 12 and outwardly therefrom through output 13 and coupler 15. As mentioned above, coupler 15 is coupled to the pulmonary arteries of the host patient. Similarly, manifold 26 is configured to receive blood flow from the host patient's pulmonary veins through coupler 24 and input 22. Within manifold 26, the turbine pump set shown below is operative to pump the incoming blood outwardly through output 23 and coupler 25 to the host patient's aorta. The configuration of redundant servomotor drives and turbine pumps within housing 11 is set forth below in greater detail in FIGS. 5 and 7. Suffice it to note here that housing 11 is generally configured to maintain a small easily implanted structure which is virtually entirely functional in its shape. It will be understood that housing 11 together with manifolds 16 and 26 as well as inputs 12 and 22 and outputs 13 and 23 are preferably fabricated of a material suitable for implanting within the host patient's body. Couplers 14, 15, 24 and 25 are configured in accordance with conventional fabrication techniques to receive appropriate connection to presently available fluid couplings and tubing apparatus utilized in heart transplant situations. It will be noted that FIG. 3 shows the use of "right-angle" type couplers for couplers 14, 15, 24 and 25. However, it will be understood that straight line couplers may be utilized such as those illustrated in FIG. 7 without departing from the spirit and scope of the present invention. The important aspect for selecting coupler configurations is directed solely at the efficiency of blood flow and the convenience with respect to implantation within the host patient's body.

Figure 4:
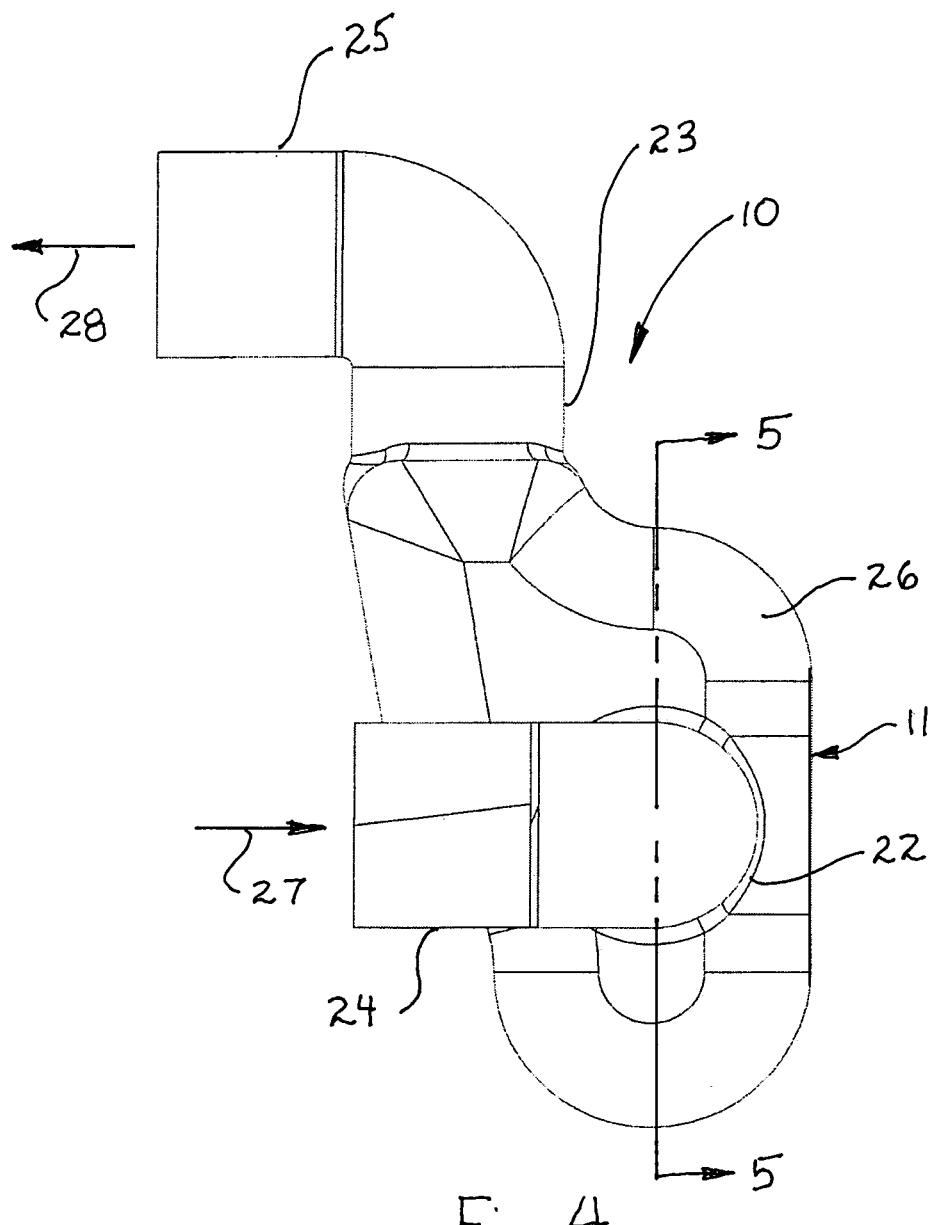
FIG. 4 sets forth a right side view of the present invention dual-stage redundant-impeller artificial heart, the left side view being a mirror image thereof.

FIG. 4 sets forth a right side view of artificial heart 10. As described above, artificial heart 10 includes a manifold 26 having an input 22 and an output 23. Coupler 24 is joined to input 22 while coupler 25 is joined to output 23. In accordance with the above-described operation, blood flows inwardly in the direction indicated by arrow 27 through coupler 24 and input 22 to the interior of manifold 26. The turbine pumps (set forth below in FIGS. 5 and 7) operative within manifold 26 draw blood inwardly in the direction indicated by arrow 27 and pump it outwardly through output 23 and coupler 25 in the direction indicated by arrow 28. As mentioned above, artificial heart 10 includes a mirror image manifold 16 (seen in FIG. 3) which operates in a substantially identical manner to the apparatus within manifold 26.

Figure 5:
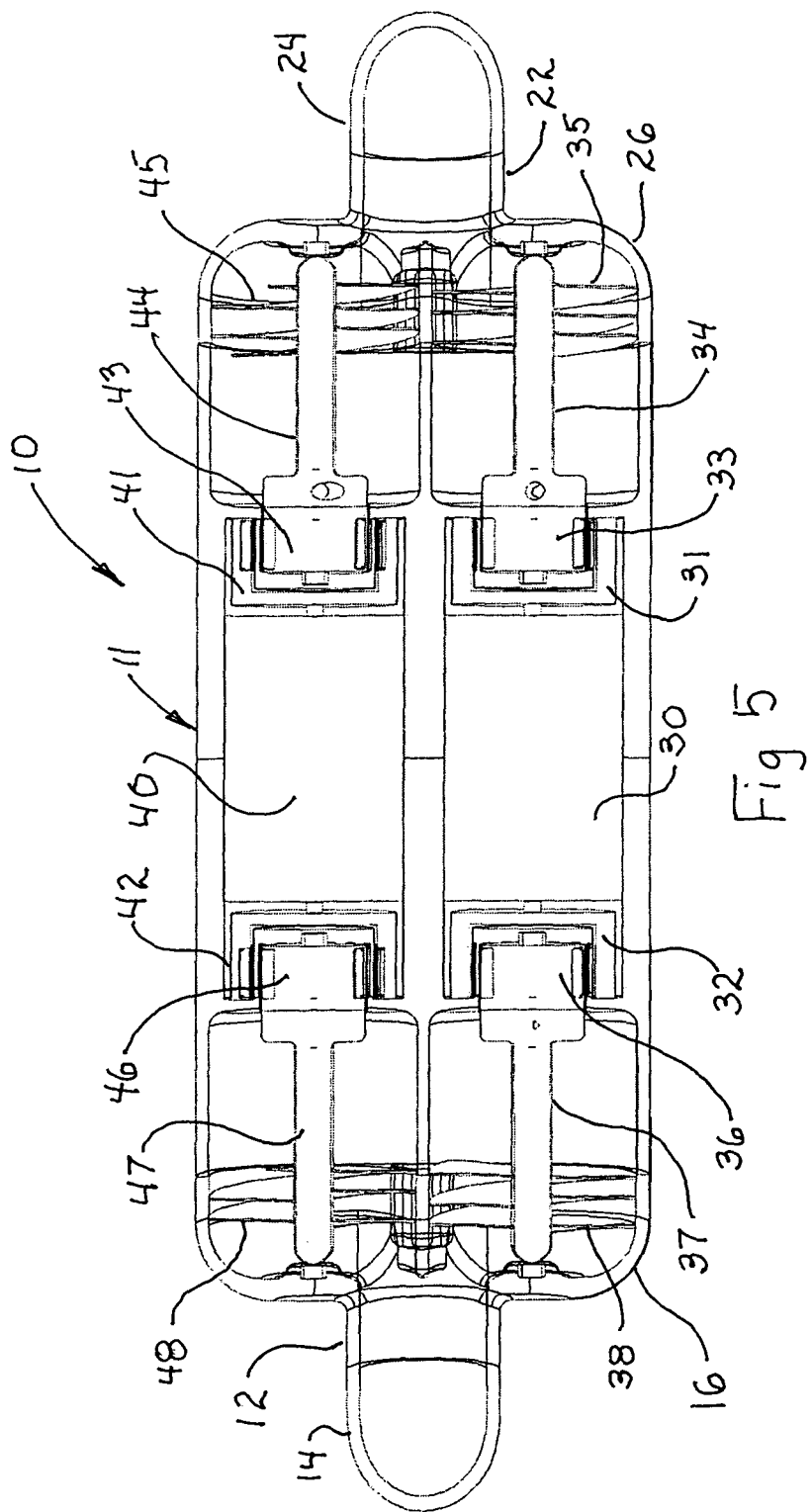
FIG. 5 sets forth a section view of the present invention dual-stage redundant-impeller artificial heart taken along section lines 5-5 in FIG. 4.

FIG. 5 sets forth a section view of artificial heart 10 taken along section lines 5-5. It will be noted that FIG. 5 is intended to provide a somewhat simplified section view in which the overall orientation and arrangement of major operative components within artificial heart 10 may be illustrated and discussed. It will be further noted that the apparatus driving the plurality of turbine pumps within artificial heart 10 shown in FIG. 5 is somewhat generalized to represent both conventional servomotor apparatus or, alternatively, a more efficient servo-type drive in which the stationery coils of the drive apparatus are molded in housing 11 and in which magnetically coupled rotors are joined to each of the turbine pump shafts. The important aspect in FIG. 5 with respect to the present invention is to observe and understand the overall physical layout and arrangement of the present invention dual-stage redundant-impeller artificial heart which achieves a heretofore unrealized reliability and performance.

More specifically and with reference to FIG. 5, artificial heart 10 includes a housing 11 supporting a pair of manifolds 16 and 26. As described above, manifold 16 supports an input 12 which in turn supports a coupler 14. Similarly, as described above, manifold 26 supports an input 22 which in turn supports a coupler 24. Housing 11 further supports a pair of servo drives 30 and 40. Servo drives 30 and 40 are substantially identical and are arranged in a top and bottom configuration. As is set forth below, each of servo drives 30 and 40 are independently operable by the system controller. Suffice it to note here that, under the operation and control of the system controller, electrical power is provided to each of servo drives 30 and 40 to produce the desired pumping activities.

Servo drive 30 is operatively coupled to a pair of magnetic couplers 31 and 32. A magnetic rotor 33 together with a turbine shaft 34 is rotatably supported within manifold 26 and housing 11 by conventional bearing means (not shown). Turbine shaft 34 further supports a plurality of turbine blades 35. Magnetic rotor 33 is operatively coupled to magnetic coupler 31 by induced magnetic coupling. Thus, a rotating magnetic field produced by magnetic coupler 31 under the influence of servo drive 30 produces a magnetically coupled energy which in turn causes magnetic rotor 33 to rotate. The rotation of magnetic rotor 33 in turn causes a corresponding rotation of turbine shaft 34 and turbine blades 35. By similar action, the rotating magnetic field produced by magnetic coupler 32 causes rotation of magnetic rotor 36 which in turn produces rotation of turbine shaft 37 and turbine blades 38.

As previously mentioned, servo drive 40 is substantially identical to servo drive 30 and is identical in operation. Accordingly, servo drive 40 includes a rotating magnetic coupler 41 at one end and a rotating magnetic coupler 42 at the opposite end. Servo drive 40 further includes a magnetic rotor 43 together with a turbine shaft 44 and a plurality of turbine blades 45 all supported by conventional bearing means (not shown) for rotation within manifold 26 and housing 11. Similarly, servo drive 40 also includes a magnetic rotor 46 which together with a turbine shaft 47 and a plurality of turbine blades 48 is supported for rotation within manifold 16 and housing 11. As mentioned, the operation of servo drive 40 is substantially identical to servo drive 30. Thus, servo drive 40 produces a rotating magnetic field within magnetic couplers 41 and 42. Under the influence of this rotating magnetic field, magnetic rotors 43 and 46 are caused to rotate. This in turn produces rotation of turbine shafts 44 and 47 together with turbine blades 45 and 48. Thus, as servo drive 40 is energized, turbine blades 45 and 48 are rotated producing the desired pumping action.

As described above, servo drives 30 and 40 may utilize conventional rotating servo motors in which case magnetic couplers 31 and 32 as well as magnetic couplers 41 and 42 are physically rotating magnetic arrays. This produces the rotating magnetic field utilized in driving magnetic rotors 33 and 36 as well as magnetic rotors 43 and 46. Alternatively, servo drives 30 and 40 may utilize embedded electromagnetic coils preferably supported within the interior of housing 11. In such case, magnetic couplers 31 and 36 as well as magnetic couplers 41 and 46 are physically stationery and provide a coupling of the rotating magnetic fields produced within the embedded coils of servo drives 30 and 40. In either event, the objective is to produce rotating magnetic fields operatively coupled to magnetic rotors 33 and 36 as well as magnetic rotors 43 and 46 to power the respective turbine blade arrays required for pumping activity.

In operation with servo drives 30 and 40 being activated under the control of the system controller (seen in FIG. 8), turbine blades 35, 38, 45 and 48 are rotated. The rotating action of the turbine blades draws blood inwardly through input 12 to the interior of manifold 16. Thereafter, the pumping action provided by turbine blades 38 and 48 described below in FIG. 6 in greater detail produces a pressurized blood flow outwardly from manifold 16. Similarly, the rotation of turbine blades 35 and 45 within manifold 26 draws blood inwardly through coupler 24 and input 22 to the interior of manifold 26. Within manifold 26, the rotation of turbine blades 35 and 45 produces a pumping action which drives blood flow outwardly through output 23 and coupler 25 (both seen in FIG. 1). In accordance with an important aspect of the present invention described below in greater details, the structures of fluid coupling paths within manifolds 16 and 26 are configured to provide operation in which both turbine blade sets are rotating under normal conditions or to provide blood flow under the drive supplied by one of the turbine blade sets. In this manner, the present invention artificial heart provides significant redundance which increases reliability. Simply stated, should either of servo drives 30 or 40 fail, the patient is sustained by blood flow provided solely by the remaining operative servo drive and its associated turbine blades. This provides an important backup redundance and will sustain the host patient until appropriate remedial action may be performed.

Figure 6:
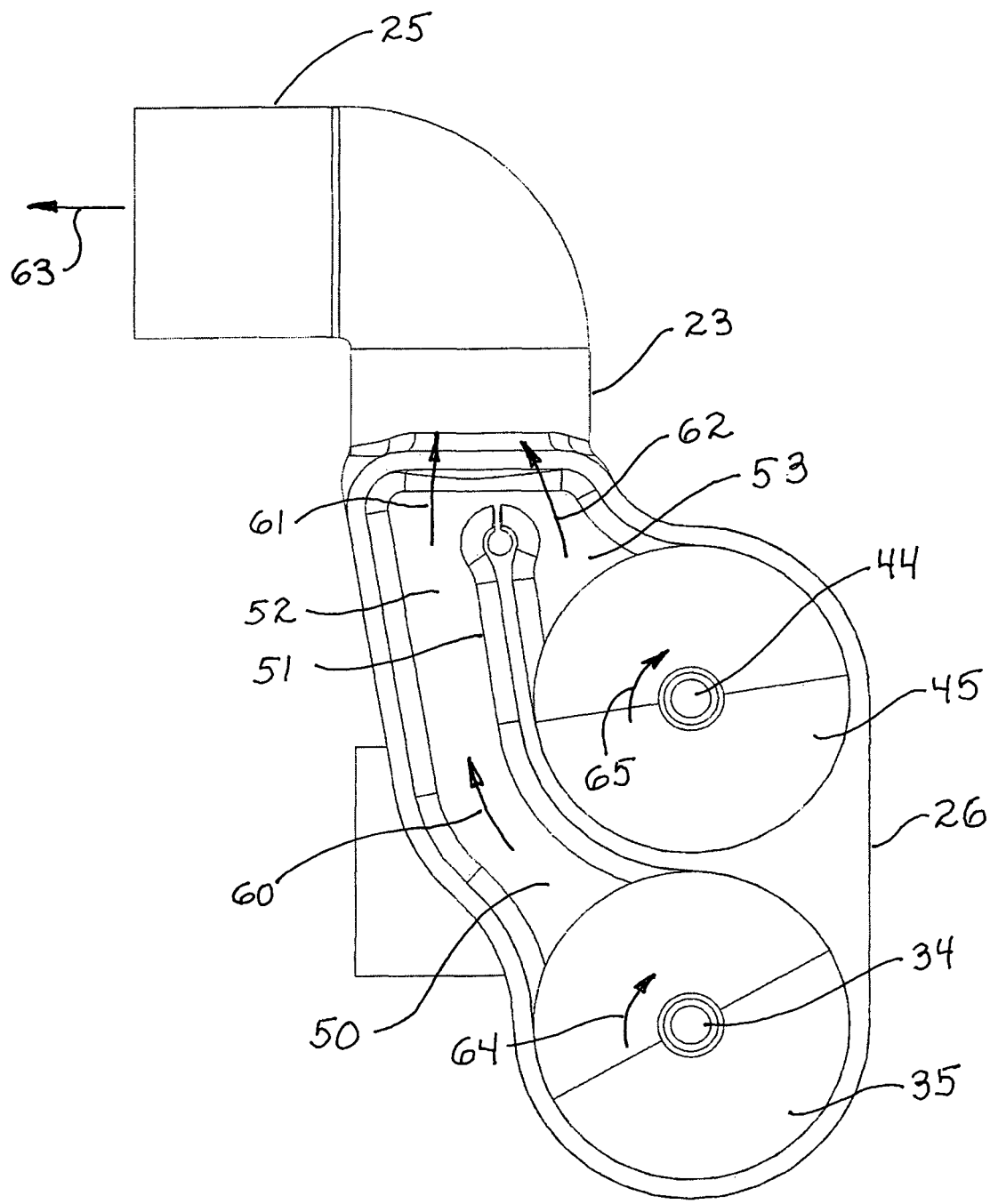
FIG. 6 sets forth a section view of the present invention dual-stage redundant-impeller artificial heart taken along section lines 6-6 in FIG. 2.

FIG. 6 sets forth a section view of artificial heart 10 taken along section lines 6-6 in FIG. 2. It will be apparent to those skilled in the art that while FIG. 6 shows the section view for manifold 26, the mirror image relationship between manifolds 26 and 16 renders the illustrations, operations and descriptions which follow in FIG. 6 for manifold 26 to be equally applicable to manifold 16.

More specifically, artificial heart 10 includes a manifold 26 which in turns defines an interior chamber 50. A curved wall 51 extends inwardly from the interior of manifold 26 and curves through interior chamber 50 to divide chamber 50 into a pair of flow paths 52 and 53. Flow paths 52 and 53 receive turbine blades 35 and 45 respectively. Flow paths 52 and 53 combine within output 23 to provide a combined flow path outwardly from manifold 26. In accordance with an important aspect of the present invention, turbine blades 35 and 45 are not isolated completely from each other. Thus, rotation of either of turbine blades 35 or 45 produces blood flow within flow paths 52 and 53. Thus, in the event of a failure of one of servo drives 30 or 40 (seen in FIG. 5), the continued rotation of either of turbine blades 35 or 45 continues to draw blood into manifold 26 and continues to pump blood flow outwardly through flow paths 52 and 53. Accordingly, a portion of the blood within manifold 26 is recirculated within manifold 26 in response to failure of either of servo drives 30 or 40 (seen in FIG. 5). This recirculation of blood within manifold 26 in the event of a failure of either servo drive provides an important safeguard against the creation of static blood pooling or collecting within manifold 26 as the system responds to failure of either of the servo drives. The creation of such static pooling areas raises substantial risk of blood clotting and its attendant problems.

During normal operation, as turbines 35 and 45 are rotated in the manner indicated by arrows 64 and 65, the turbine pumping action produces blood flow into manifold 26 via input 22 and coupler 24 (seen in FIG. 4). This blood flow drawn into manifold 26 divides under the influence of turbines 35 and 45 and is pumped outwardly through flow paths 52 and 53 respectively forming blood flow as indicated by arrows 60, 61 and 62. The combined blood flow traveling through flow paths 52 and 53 joins within output 23 and coupler 25 to provide a total outflow as indicated by arrow 63. Thus, under normal operation, blood is drawn into manifold 26 by the action of turbine blades 35 and 45 and is pumped outwardly through flow paths 52 and 53. During failure of either pump (seen in FIG. 5), blood continues to be drawn into manifold 26 by either of turbine blades 35 or 45 and continues to be pumped outwardly through output 23. As mentioned, in the event of a servo drive failure, the recirculation occurring in response to the remaining operative turbine blade set includes a recirculating component of blood flow to avoid pooling and potential blood clotting.

Once again, it must be remembered that the descriptions and illustrations in connection with FIG. 6 which set forth the operation of manifold 26 together with turbines 35 and 45 is equally descriptive of the operations of turbines 38 and 48 operative within manifold 16 (seen in FIG. 5). In the preferred fabrication of the present invention in which output 13 and coupler 15 (seen in FIG. 1) are coupled to the host patient's pulmonary arteries while output 23 is coupled to the host patient's aorta, the pumping characteristics of turbine blades 38 and 48 are preferably different that turbine blades 35 and 45. This difference in pumping characteristics is required due to the difference in pumping pressure between the host patient's pulmonary arteries and the host patient's aorta. Accordingly, different pumping characteristics may be provided by altering the characteristics of each of the turbine blade sections within artificial heart 10.

Figure 7:
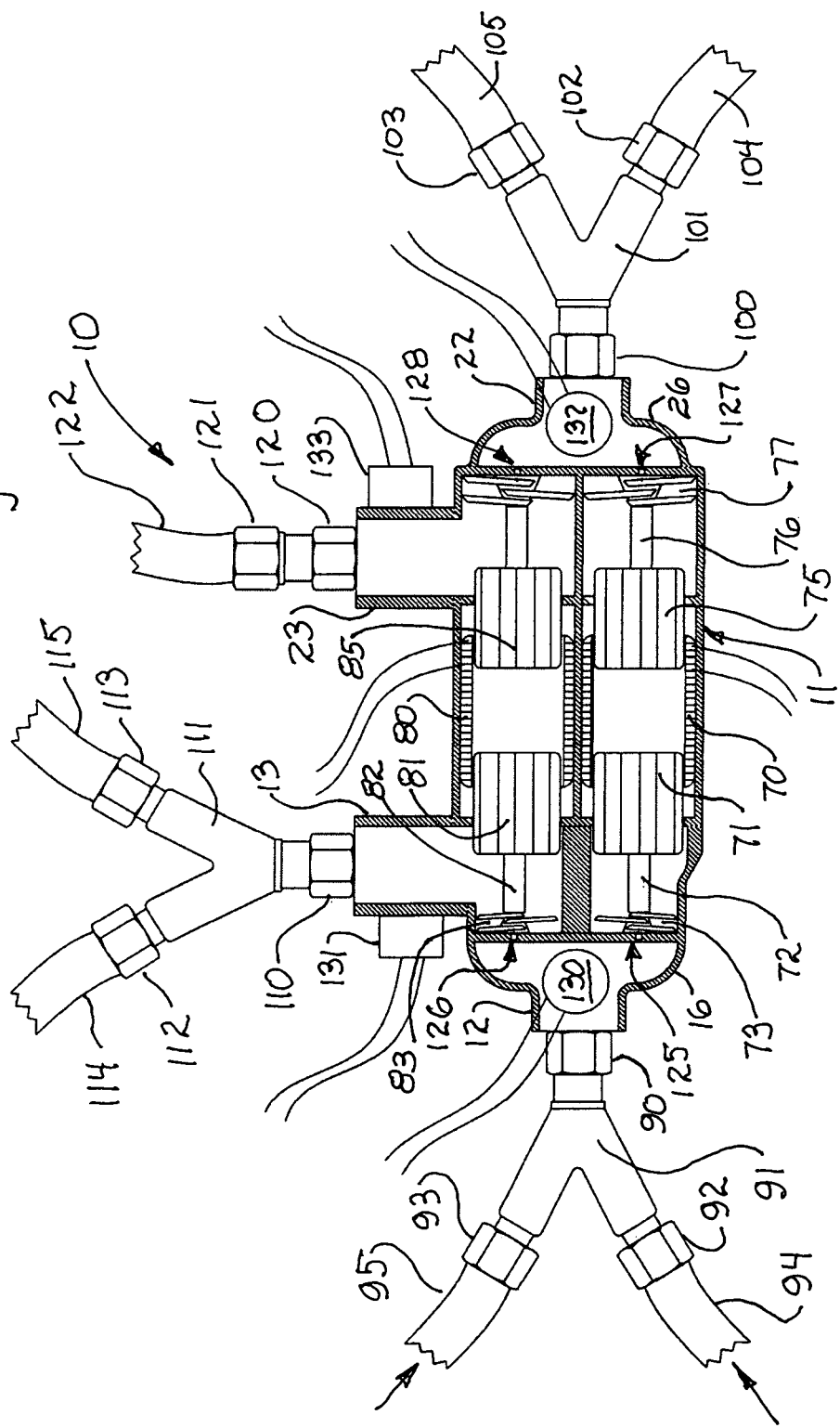
FIG. 7 sets forth a simplified section view of the present invention dual-stage redundant-impeller artificial heart showing couplings to the recipient's circulatory and pulmonary systems.

FIG. 7 sets forth a simplified section view of the present invention artificial heart showing illustrative blood flow connections to the host patient's circulatory system. It will be noted that in the section view of FIG. 7, the servo drive apparatus utilize embedded electrical coils supported within the housing interior to produce the rotating magnetic field used to drive the pumping apparatus. With temporary reference to FIG. 5, the contrast in the servo drive apparatus physical structure may be noted since FIG. 5 is more illustrative of a conventional servo motor drive. Returning to FIG. 7, artificial heart 10 includes a housing 11 supporting a pair of manifolds 16 and 26 on opposite ends thereof. Housing 11 further includes inputs 12 and 22 together with outputs 13 and 23. Artificial heart 10 includes a pair of servo drives 70 and 80 which comprise motor coil windings supported within the interior of housing 11. In the preferred fabrication of housing 11, and servo drives 70 and 80, the electromagnetic windings which comprise servo drives 70 and 80 are molded into the material of housing 11. Artificial heart 10 further includes a pair of magnetic rotors 71 and 75 supported within the interior of housing 11 and positioned to be rotatably supported in magnetic coupling to turbo drive 70. Magnetic rotors 71 and 75 further support turbine shafts 72 and 76 respectively. The ends of turbo shafts 72 and 76 support respective turbines 73 and 77. Thus, the combination of magnetic rotor 71, turbine shaft 72 and turbine 73 are supported for rotation by conventional bearing means (not shown). Similarly, the combination of magnetic rotor 75, turbine shaft 76 and turbine 77 are also supported for rotation by bearing means (not shown).

Artificial heart 10 further includes a pair of magnetic rotors 81 and 85 supported within the interior of housing 11 and positioned within servo drive 80. Magnetic rotor 81 is joined to turbine shaft 82 which in turn supports turbine 83 the combination of which is rotationally supported by conventional bearing means (not shown). Similarly, a magnetic rotor 85 together with a turbine shaft 86 and turbine 87 are rotationally supported within the interior of housing 11 by conventional bearing means (not shown).

Manifold 16 includes an input 12 and receives turbines 73 and 83. A pair of openings 125 and 126 formed within the interior of manifold 16 facilitate blood flow entering through input 12 to turbines 73 and 83. Similarly, manifold 26 defines an input 22 which receives turbines 77 and 87. By way of further similarity, manifold 26 defines a pair of openings 127 and 18 which facilitate blood flow into manifold 26 through input 22 which thereafter is drawn through openings 127 and 128 under the influence of turbines 77 and 87. Housing 11 further includes a pair of outputs 13 and 23 which are operatively coupled in fluid communication with the interior of manifolds 16 and 26 respectively.

In operation, the system controller (seen in FIG. 8) applies suitably configured electrical drive signals to servo drives 70 and 80. The currents within servo drives 70 and 80 produce rotating magnetic fields which in turn produce rotation of magnetic rotors 71 and 75 within servo drive 70 and magnetic rotors 81 and 85 within servo drive 80. As each magnetic rotor is caused to rotate by the rotating magnetic fields corresponding rotation takes place for turbine shafts 72 and 76 as well as shafts 82 and 86. Shaft rotation produces a corresponding rotation of turbines 73 and 77 as well as turbines 83 and 87. Thus, as servo drives 70 and 80 are energized, the rotating magnetic fields therein drives the magnetic rotors which in turn produces rotation of the turbines. As a result, with both servo drives 70 and 80 functioning, blood is drawn into manifold 16 through input 12 and is pumped outwardly therefrom through output 13. Correspondingly, blood is drawn into manifold 26 through input 22 and is pumped outwardly therefrom through output 23. To facilitate the desired control of pump operation, a plurality of pressure sensors are situated at selected locations within artificial heart 10. These sensors are preferably pressure responsive transducers which are conventional is design and which are characterized by producing electrical signals which are then coupled to the system controller (seen in FIG. 8). While the location and selection of the types and numbers of sensors may be to some extent a matter of design choice or need, it has been found opportune to provide sensor 130 within manifold 16 proximate input 12 and to provide sensor 132 within manifold 26 proximate input 22. Similarly, it has been found advantageous to place a sensor 131 proximate output 13 and a sensor 133 proximate output 23. With this relatively straight forward array of sensors, the system controller can receive signals which indicate the pressure of flow into each of manifolds 16 and 26 and the pressure output from outputs 13 and 23. This in turn facilitates a basic monitoring of pump performance. Additional sensors may be placed within artificial heart 10 as desired to perform other functions such as monitoring the performance of the servo drive apparatus.

FIG. 7 also shows a coupling diagram by which artificial heart 10 is joined to the host patient's circulatory system. Thus, in the example of FIG. 7, a coupler 90 is joined to input 12 which in turn is coupled to a split coupler 91. Split coupler 91 in turn is coupled to a pair of tubes 94 and 95 by conventional couplings 92 and 93. Tubes 95 and 94 are coupled to the host patient's superior vena cava and inferior vena cava respectively. Output 13 is coupled to a split coupler 111 by a conventional coupler 110. Split coupler 111 in turn is joined to a pair of tubes 114 and 115 by conventional couplers 112 and 113 respectively. Tubes 114 and 115 are joined to the pulmonary arteries of the host patient. Input coupler 100 is joined to a split coupler 101. Split coupler 101 is joined to a pair of tubes 104 and 105 by conventional couplings 102 and 103 respectively. Tubes 104 and 105 are coupled to the host patient's pulmonary veins. Finally, output 23 is coupled to a tube 122 by couplers 120 and 121. Tube 122 is coupled to the host patient's aorta.

Thus, during normal operation within both servo drives 70 and 80 functioning, returning blood from the patient's superior vena cava and inferior vena cava is drawn into manifold 16 and under the influence of turbines 73 and 83 is pumped upwardly through output 13 to the host patient's pulmonary arteries. Blood returning from the patient's lungs through the patient's pulmonary veins is carried by tubes 104 and 105 together with split coupler 101 to be drawn into manifold 26 through input 22. Thereafter, under the influence of turbines 77 and 87, the blood is further pumped outwardly through output 23 to tube 122 and thereafter to the host patient's aorta. Thus, artificial heart 10 functions to draw returning blood from the patient's body, pump the blood into the patient's pulmonary arteries, draw the oxygenated blood from the host patient's lungs to the second pumping stage after which the blood is pumped out to the patient's body to complete the circulation.

In accordance with an important aspect of the present invention, the use of redundant servo drives for the pumping functions of artificial heart 10 provides a dramatic improvement in the overall system reliability achieved. This reliability is further enhanced by the system design which provides that in the event of a failure of either of servo drives 70 or 80, the remaining operative servo drive is able to sustain the patient's life until remedial action can be accessed and undertaken. In the event the system is operating on one active servo drive, the structure of manifolds 16 and 26 provides for a recirculation of blood within the manifolds to avoid stagnation and blood pooling which might otherwise lead to a clotting condition.

Figure 8:
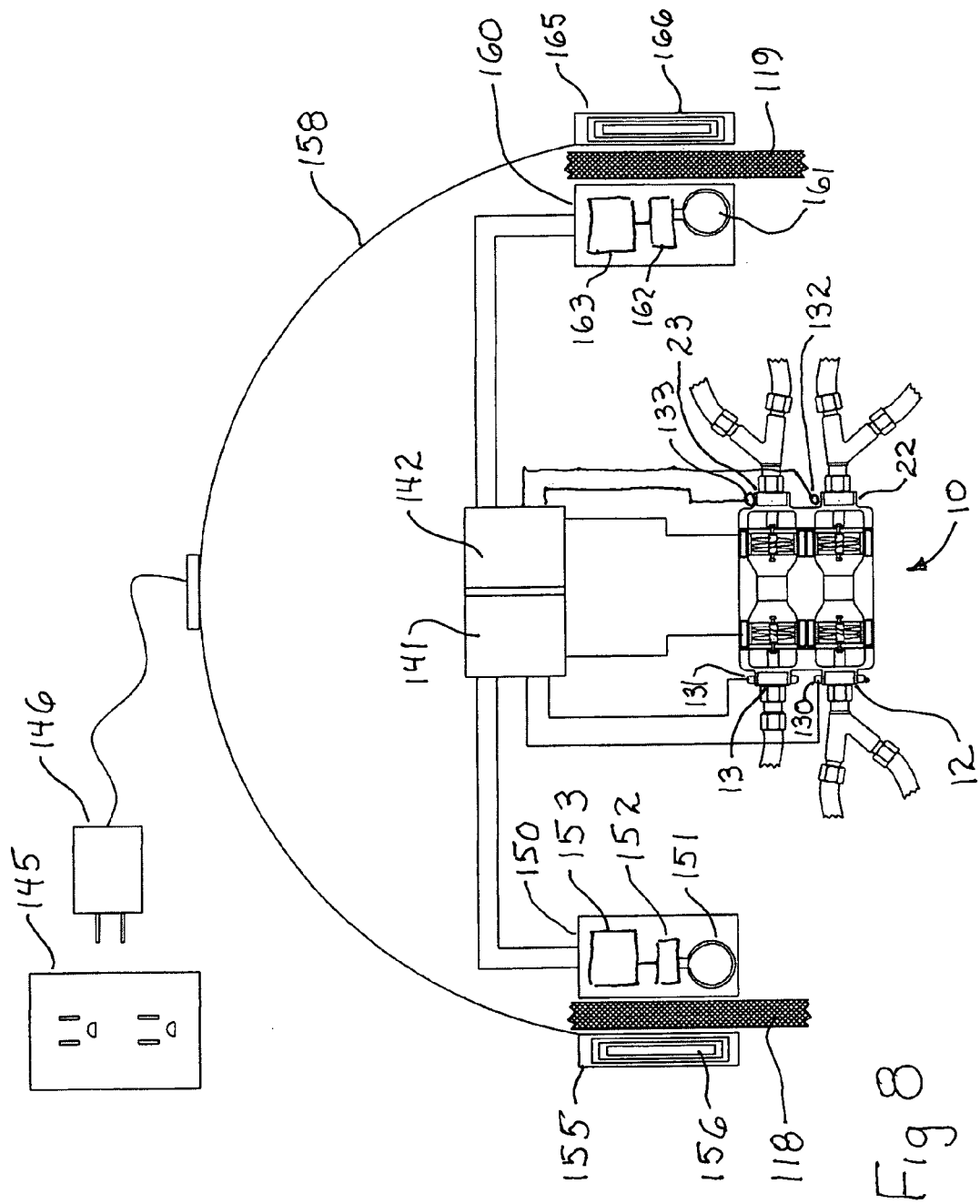
FIG. 8 sets forth a schematic layout of the major components of the present invention battery-power and charging apparatus of the present invention dual-stage redundant-impeller artificial heart.

FIG. 8 sets forth a block diagram of the present invention artificial heart in a typical surrounding environment. In the situation represented in FIG. 8, artificial heart 10 has been implanted within a host patient's body and is operatively coupled in the manner set forth above in FIG. 7 to the host patient's circulatory system. FIG. 8 further shows a microcontroller unit 140 also implanted within the host patient's body. Microcontroller unit 140 is formed of a pair of fully redundant micro controllers 141 and 142. The redundancy of micro controllers 141 and 142, each able to fully support the operation of artificial heart 10 provides a further measure of reliability. Microcontroller unit 140 further includes conventional apparatus (not shown) for communicating to the exterior of the host patient's body in order to provide alarm condition information or other required maintenance of monitoring information to an external unit (not shown). As described above, artificial heart 10 includes a plurality of sensors 130, 131, 132 and 133 situated at the respective inputs and outputs of artificial heart 10. Sensors 130 through 133 are coupled to redundant microcontrollers 141 and 142. Microcontroller 142 further includes additional sensors supported within artificial heart 10 for monitoring the performance of the servo drive apparatus therein. A pair of battery units 150 and 160 are also implanted within the host patient. Battery unit 150 includes a secondary charging coil 151 coupled to a rectifier 152 which in turn is coupled to a battery 153. Battery unit 150 is coupled to microcontroller 141. Similarly, battery unit 160 includes a charging coil 161 coupled to a rectifier 162 which in turn is coupled to a battery 163. By way of further similarity, battery unit 160 is operatively coupled to microcontroller 142. Thus, microcontrol unit 140, artificial heart 10 and battery units 150 and 160 together with appropriate wire connections therebetween are implanted within a host patient body. For purpose of illustration, FIG. 8 shows body segments 118 and 119 which represent the skin and associated tissues of the host patient body beneath which battery units 150 and 160 are implanted. Preferably units 150 and 160 are implanted near the host patient's mid section and preferably situated just beneath the patient's skin.

A charging belt 158 suitably configured to be worn by the host patient such as at or near the patient's waist supports a pair of charging units 155 and 156. Charging units 155 and 165 include respective primary charging coils 156 and 166. Coils 156 and 166 are coupled to source of alternating current power such as a conventional electrical outlet 145 via a conventional coupling adapter 146.

In operation, micro controller 141 and 142 monitor the plurality of sensors within artificial heart 10 and provide suitable operating power and control to the servo drives supported therein (seen in FIG. 5). Microcontrollers 141 and 142 utilize batteries 153 and 163 for operative battery supply and for power to energize the servo drive apparatus within artificial heart 10. The operative power stored within batteries 153 and 163 is provided by inductive charging utilizing charging units 155 and 165. Thus, during convenient periods, the host patient utilizes charging belt 158 by coupling to power source 145 while wearing belt 158 such that primary charging coils 156 and 166 are positioned on the outside of body portions 118 and 119 respectively such that general alignment is obtained between primary charging coils 156 and 166 and secondary coils 151 and 161 respectively. Electrical power is then inductively coupled through body portions 118 and 119 to induce alternating current power within secondary coils 151 and 161. Rectifiers 152 and 162 convert the alternating current induced in coils 151 and 161 to a direct current power suitable for charging batteries 153 and 163. In this manner, the user is able to replenish the battery energy as required by simply wearing charging belt 158 for a suitable time interval.

Micro controller unit 140 functions using a pair of fully-redundant fully-interconnected micro controllers, each having the complete capability to control and run the entire artificial heart system and it's monitoring and charging functions. Thus, micro controllers 141 and 142 provide inputs for two batteries, inputs for multiple pressure and Hall effect servo sensors and systems capable of monitoring multiple battery charge levels and switch between batteries. The redundancy of micro controllers 141 and 142 includes configuration of the system such that each micro controller "sees" all it's own inputs and also "sees" all inputs to the other micro controller. This redundancy includes each micro controller being capable of making compensating performance adjustments to maintain envelope system performance. However, to avoid "hunting" between the redundant micro controllers, it is preferred that small pressure variations of each pump be allowed before adjustment is made.

Micro controller unit 140 further includes communication capability, such as a wireless unit, to call, or text remote locations to indicate system anomalies, failures, operating conditions, battery charge levels and other conditions. In addition, micro controller unit 140 provides the capability to adjust each of micro controllers 141 and 142 based on pressure readings and to set and maintain preset maximum and minimum pressure envelopes.

Micro controller unit 140 also provides the ability of replicating the pulsitile operation characteristic of a normal human heart by introducing pre-programmed increases and decreases of pump speed to create pressure surges and lulls.

Figure 9:
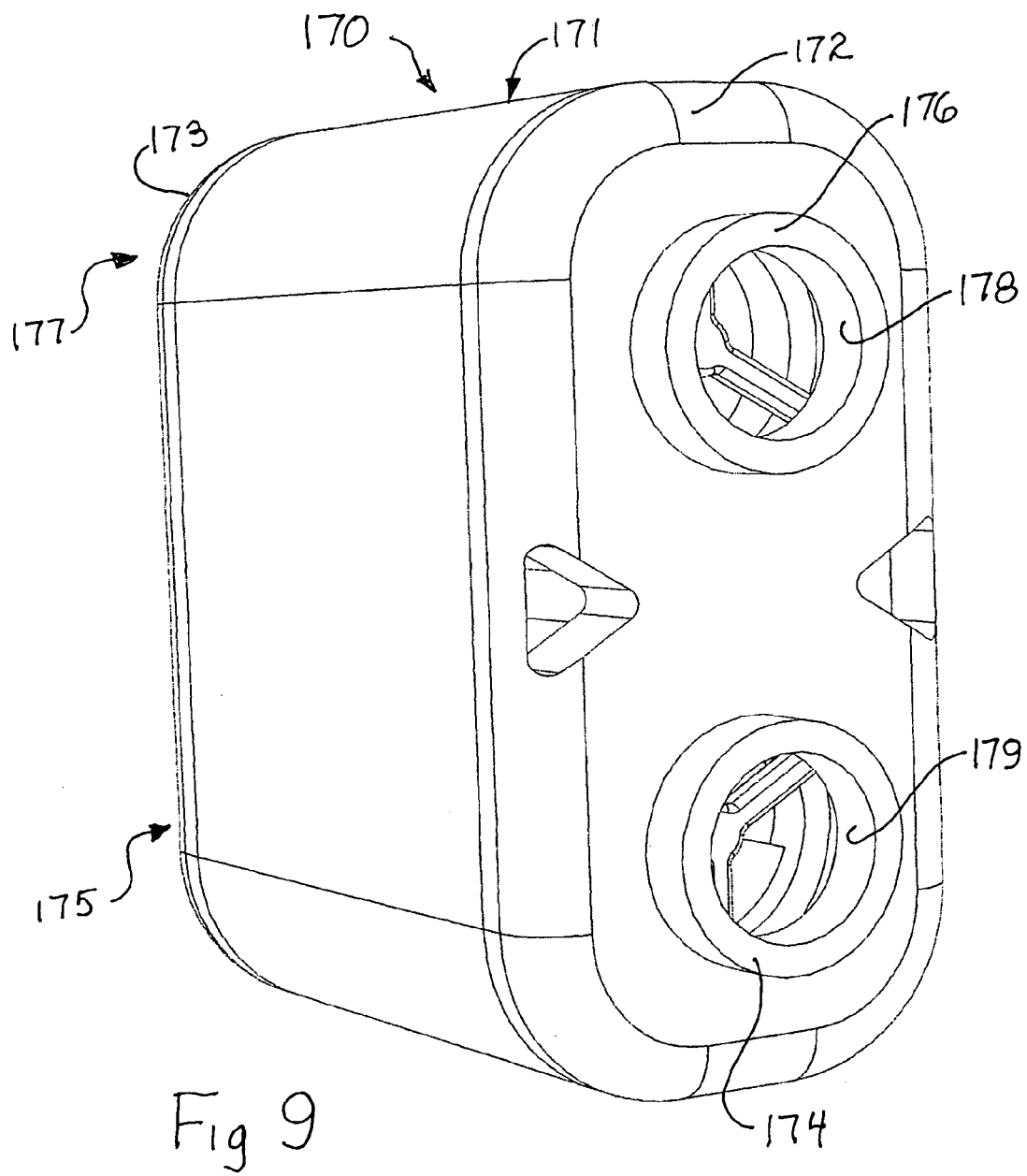
FIG. 9 sets forth a perspective view of an alternate embodiment of the present invention artificial heart.

FIG. 9 sets forth a perspective view of an alternate embodiment of the present invention dual-stage redundant-impeller artificial heart constructed in accordance with the present invention and generally referenced by numeral 170. Artificial heart 170 is fabricated in general correspondence to artificial heart 10 described above and set forth in FIGS. 1 through 8. Thus, artificial heart 170 provides multiple turbine pump stages in the same general manner described above in artificial heart 10 and utilizes the redundancy provided by such multiple turbine pump stages. However, as will be seen in the figures and descriptions which follow, artificial heart 170 utilizes a "flow through" design which further improves the blood flow through the pump stages and the blood flow between the pump stages to provide increased efficiency and a further protection against the stagnation or pooling of blood within the artificial heart. This is extremely important in that blood which is allowed to pool or stagnate within the artificial heart raises the potential for injurious or even fatal clotting of blood within the recipient's circulatory system. To avoid such problems, artificial heart 170 utilizes a direct flow through configuration which does not provide areas of potential of blood stagnation or blood pooling.

More specifically, FIG. 9 sets forth artificial heart 170 having a center housing 171 supporting a pair of manifolds 172 and 173 on opposite ends thereof. Manifold 172 includes an input coupling 76 defining an input passage 178 therein. Similarly, manifold 172 includes an input coupling 174 defining an input passage 179. As is better seen in FIG. 13, manifold 173 is constructed in a similar fashion to manifold 172 and thus defines a pair of output couplings 175 and 177 which define respective output passages 180 and 181. Returning to FIG. 9, in the preferred fabrication of artificial heart 170, manifolds 172 and 173 are fitted to center housing 171 after the internal pump components (shown below) are assembled within housing 171. In the preferred fabrication of the present invention, housing 171 as well as manifolds 172 and 173 are formed of a suitable medically approved plastic material. Thus, manifolds 172 and 173 are secured to housing 171 utilizing an approved method of fabrication such as thermal or sonic welding. Alternatively, assembly of manifolds 172 and 173 to housing 171 may be secured utilizing adhesive attachments or, in some circumstances, medically approved fasteners. Of importance to note in determining the assembly of manifolds 172 and 173 to housing 171 is the provision of a stable, secure and reliable attachment therebetween such that artificial heart 170 becomes, in essence, a single integral housing supporting the internal turbine pumps (shown below).

Figure 10:
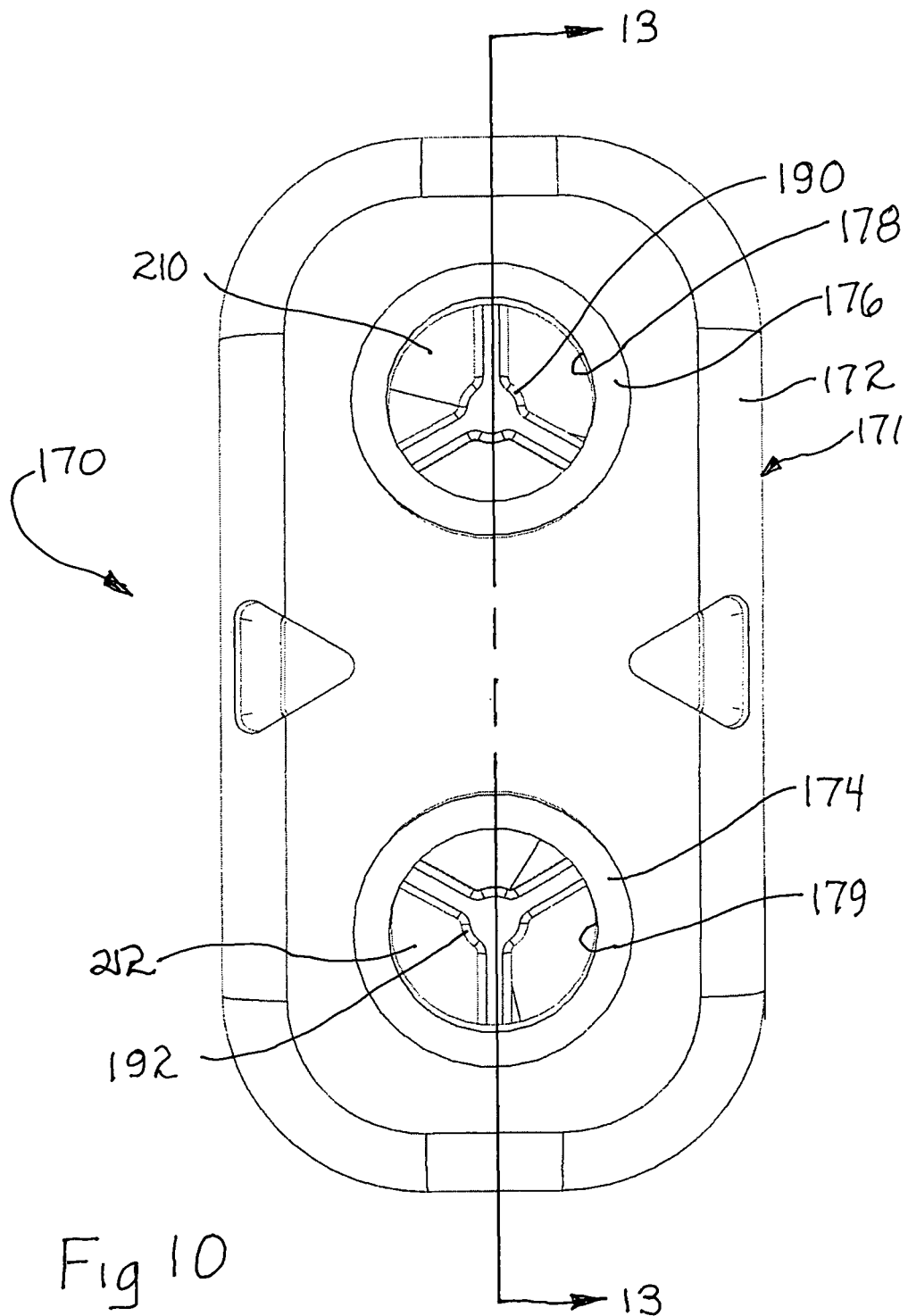
FIG. 10 sets forth an end view of the alternate embodiment of the present invention shown in FIG. 9.

FIG. 10 sets forth an end view of artificial heart 170 showing manifold 172 secured to center housing 171 (better seen in FIG. 9). As described above, manifold 172 supports a pair of input couplers 176 and 174. As is also described above, input couplers 176 and 174 define respective input passages 178 and 179. In the end view of artificial heart 170 shown in FIG. 10, portions of bearing supports 190 and 192 together with portions of turbines 210 and 212 may be seen through input passages 178 and 179. While the structure of the turbine pump segments within artificial heart 170 is shown below in greater detail, suffice it to note here that the direct flow which occurs through input passages 178 and 179 passing through bearing supports 190 and 192 respectively and into turbine pump sections 210 and 212. This fabrication in repeated on the opposite side of housing 171 in the configuration of manifold 173 (seen in FIG. 9). Suffice it to note here that as turbines 210 and 212 are rotated under the influence of magnetically coupled drive apparatus (seen in FIG. 13), the rotation of turbines 210 and 212 draws blood through passages 178 and 179 into the interior of artificial heart 170.

Figure 11:
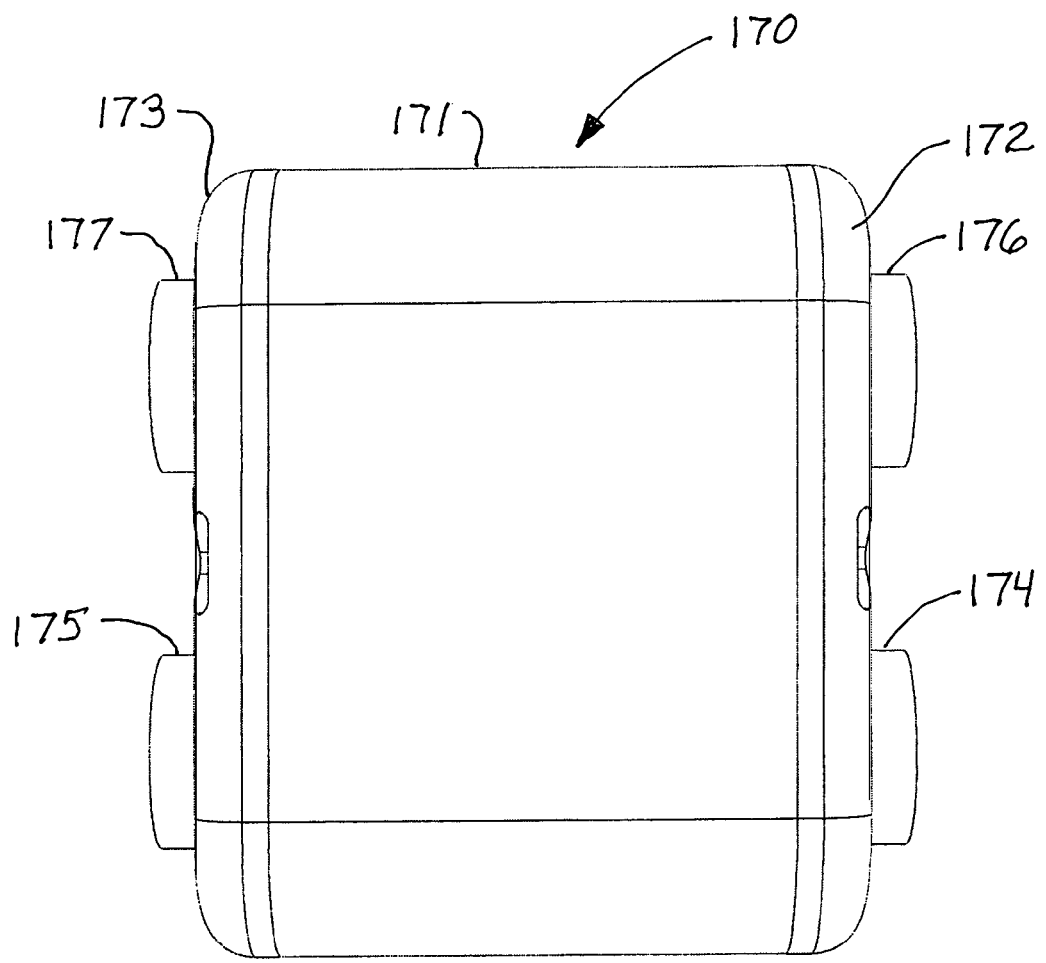
FIG. 11 sets forth a front view of the alternate embodiment of the present invention shown in FIG. 9.

FIG. 11 sets forth a front view of artificial heart 170 showing center housing 171 supporting manifolds 172 and 173. As described above, manifold 172 supports input couplers 176 and 174 while manifold 173 supports output couplers 177 and 175. As is better shown below in FIG. 14, couplers 176 and 174 are coupled to provide blood flow inputs to pump 170 while couplers 177 and 175 are utilized in providing blood flow outputs for pump 170.

Figure 12:
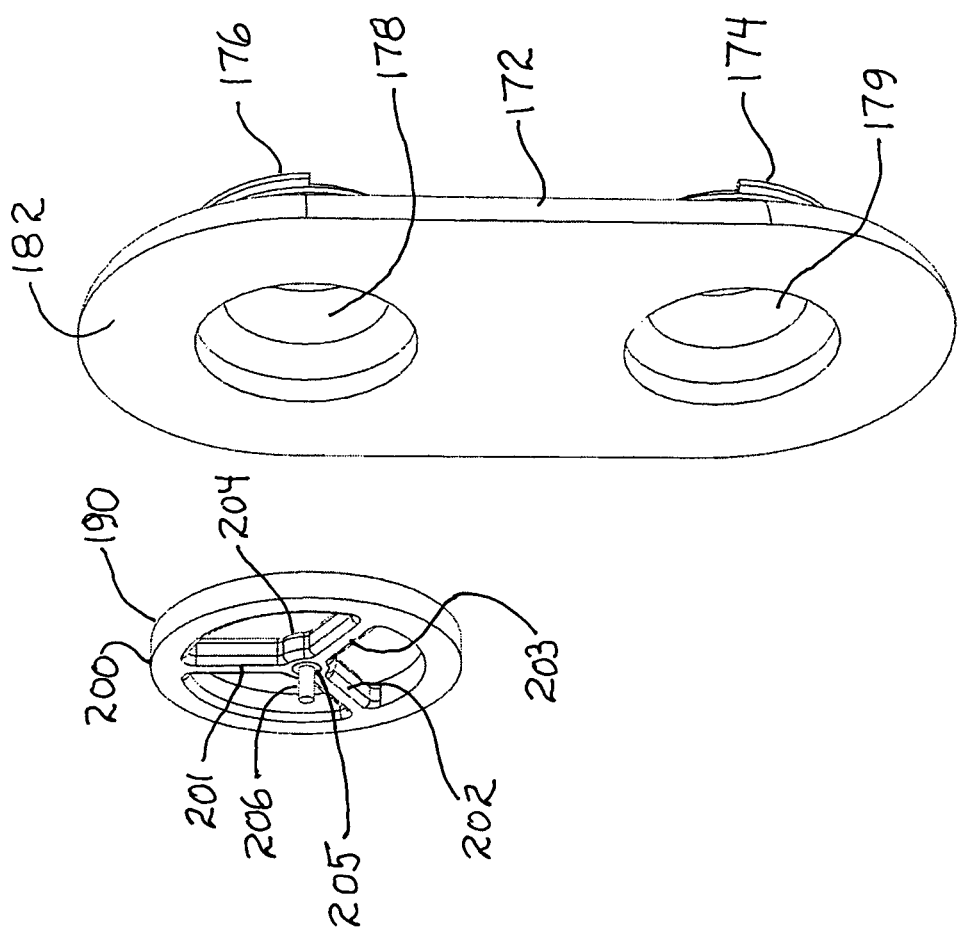
FIG. 12 sets forth a section view of the manifold and bearing support of the embodiment of the present invention shown in FIG. 9.

FIG. 12 sets forth a partial perspective assembly view of manifold 172 and bearing support 190. As described above, manifold 172 includes input couplers 176 and 174 defining respective input passages 178 and 179. Manifold 172 also defines a generally planar face 182 which in the assembly of the present invention artificial heart is positioned against housing 171 (seen in FIG. 11). FIG. 12 also shows bearing support 190 in perspective view. Bearing support 190 is representative of the plurality of bearing supports utilized in fabricating artificial heart 170. Thus, with temporary reference to FIG. 13, it will be noted that this plurality of bearing supports includes bearing supports 190 through 197. Accordingly, it will be understood that the structure of bearing support 190 set forth herein is equally descriptive of the structure of bearing supports 191 through 197 shown in FIG. 13.

Returning to FIG. 12, bearing support 190 includes a cylindrical outer rim 200 having a plurality of inwardly extending radial spokes 201, 202 and 203 which in turn meet at and support a center hub 204. Center hub 204 receives a bearing cup 205 which in turn receives a bearing pin 206. As is better seen in FIG. 13, bearing cup 205 and bearing pin 206 cooperate to support one end of turbine 210. During the course of assembly set forth below, it will be apparent that bearing support 190 is captivated within housing 171 (seen in FIG. 13) against face 182.

Figure 13:
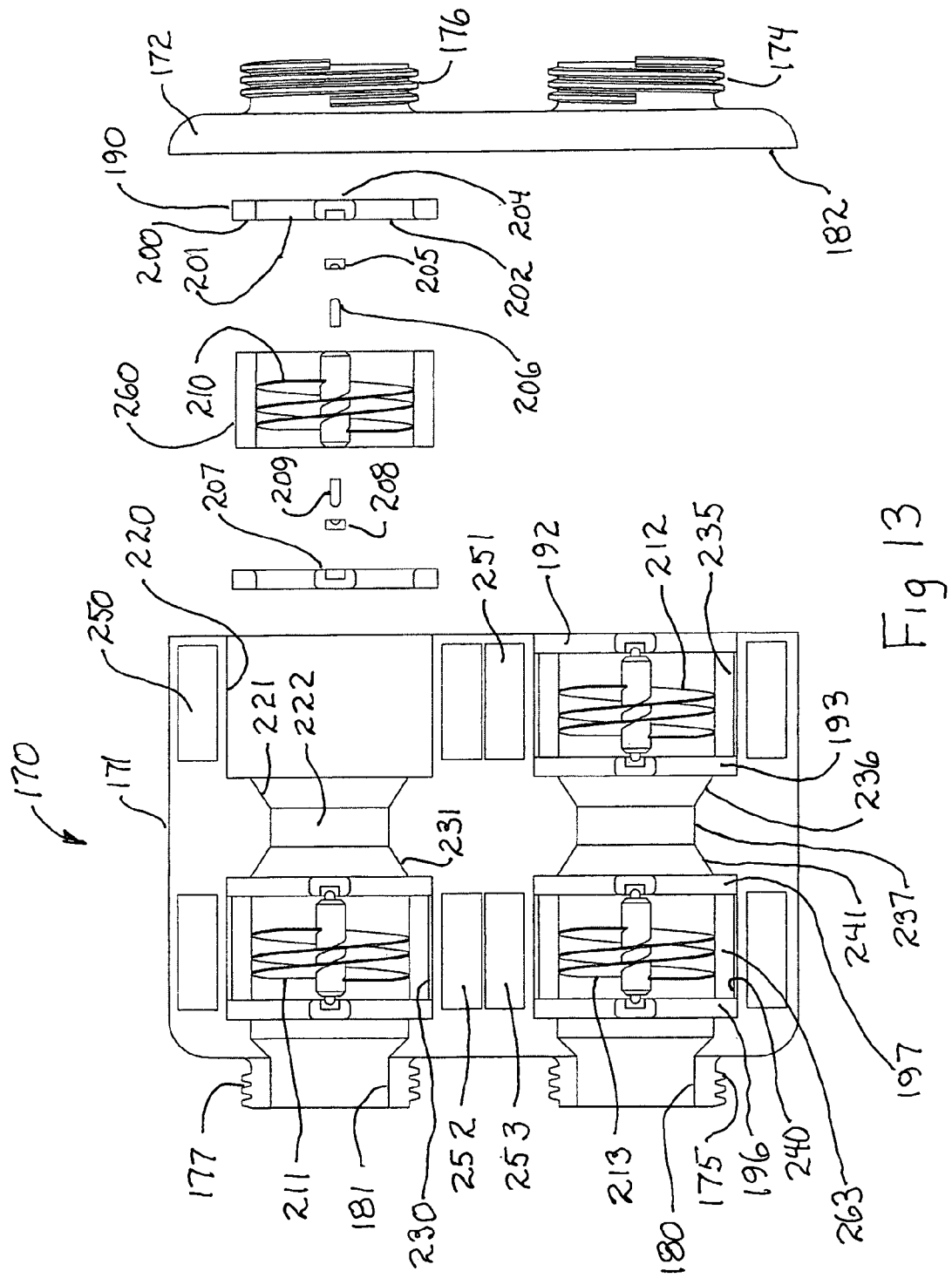
FIG. 13 sets forth a partial assembly section view of a representative pump turbine section utilized in the alternate embodiment of the present invention alternate embodiment taken along section lines 13-13 in FIG. 10.

FIG. 13 sets forth a partial section partial assembly view of artificial heart 170. In particular, FIG. 13 shows an assembly view of the structure for turbine pump 210. It will be apparent to those skilled in the art that the structure described for pump 210 is identical to the structure utilized for turbines 211, 212 and 213. Accordingly, the descriptions set forth herein for the supporting structure and drive apparatus for turbine 210 will be understood to apply equally well to the structure and drive apparatus of turbines 211, 212 and 213.

More specifically, turbine 210 is preferably fabricated to provide a helical blade progressive to form a helix. Turbine 210 further supports a cylindrical magnetic rotor 260 which is joined to the outer edges of turbine 210. Magnetic rotor 260 supports a plurality of permanent magnets and together with turbine 210 forms a single preferably integrally fabricated rotating component. Thus, for example, it will be recognized that while turbine 210 may be precision-fitted within magnetic rotor 260 due to the cylindrical structure of magnetic rotor 260 to form a single rotating unit, in the preferred fabrication of the present invention magnetic rotor 260 is integrally formed and molded with turbine 210. In either event, it will be recognized that the combined structure of turbine 210 and magnetic rotor 260 forms a single integral rotating unit. The combined structure of magnetic rotor 260 and turbine 210 are rotatably supported within the interior of housing 171 by a pair of bearing supports 190 and 191 positioned on each side of the rotating turbine element. The structure of bearing supports 190 and 191 is set forth above in FIG. 12. Thus, bearing support 190 includes a center hub 204 supported by a plurality of spokes 201, 202 and 203 (spoke 203 seen in FIG. 12). Within hub 204, a bearing cup 205 is supported which in turn receives one end of a bearing pin 206.

Bearing support 191 is identical to bearing support 190 and thus includes a center hub 207 which receives a bearing cup 208 and bearing pin 209. During assembly, bearing support 191 receives bearing cup 208 and is inserted in turbine receptacle 220 formed in housing 171. Thereafter, bearing pins 206 and 209 are inserted into the support shaft of turbine 210. The combined structure of turbine 210 supporting bearing pins 206 and 209 together with magnetic rotor 260 is then inserted into turbine receptacle 220. Bearing support 190 is then fitted within turbine receptacle 220 such that bearing pin 260 is received within bearing cup 205. The remaining turbine segments are each assembled within their respective turbine receptacles into housing 171. Once the turbine and magnetic rotor combination have been assembled within housing 171, manifolds 172 and 173 are joined to center housing 171 using an attachment such as thermal or sonic welding or other appropriate attachment. Once manifolds 172 and 173 are assembled to center housing 171, the structure of artificial heart 170 is complete and the resulting pump structure may be described.

More specifically, artificial heart 170 includes a center housing 171 defining a plurality of turbine receptacles 220, 230, 235 and 240. Receptacles 220 and 230 are aligned coaxially and define cylindrical receptacles. Turbine receptacles 220 and 230 are coupled by a venturi coupling passage formed by a tapered portion 221, a center passage 222 and a tapered portion 231 which are also generally coaxial with turbine receptacles 220 and 230.

Turbine receptacles 235 and 240 are coaxially aligned and define cylindrical receptacles. Turbine receptacles 235 and 240 are coupled by a coaxial venturi portion formed by a tapered portion 236, a coupling portion 237 and a tapered portion 241.

Housing 171 further supports a generally cylindrical drive coil array 250 which encircles turbine receptacle 220. Drive coil assembly 250 provides a motor drive coil which is molded into housing 171. Drive coil 250 is coupled to a motor controller such as controller 140 set forth above in FIG. 8. Similarly, housing 171 supports a corresponding drive coil 252 which encircles turbine receptacle 230 and a drive coil 251 which encircles turbine receptacle 235 together with a drive coil 253 which encircles turbine receptacle 240. Drive coils 250, 251, 252 and 253 are substantially identical in fabrication.

Artificial heart 170 includes a turbine 210 and magnetic rotor 260 joined to form a single rotating structure which is rotatably supported within turbine receptacle 220 by bearing supports 190 and 191. Artificial heart 170 further includes a turbine 212 and magnetic rotor 261 also joined to form a single rotating structure which is rotatably supported within turbine receptacle 235 by bearing supports 192 and 193. Artificial heart 170 further includes turbine 211 and magnetic rotor 262 joined to form a single rotating structure which is rotatably supported within turbine receptacle 230 by bearing supports 194 and 195. Finally, artificial heart 170 further includes turbine 213 and magnetic rotor 263 joined to form a single rotating structure which is rotatably supported within turbine receptacle 240 by bearing supports 196 and 197.

Thus, it will be appreciated that artificial heart 170 utilizes four turbine pump stages arranged in two series coupled pairs. It will be equally well appreciated that each of the four pump stages operative within turbine receptacles 220, 230, 235 and 240 includes a drive coil supported within housing 171 and a rotating rotor formed by the combination of a turbine and a magnetic rotor. The resulting combination are often referred to in the art as "frameless servo motors". However, it will be apparent to those skilled in the art that other servo motor drive structures may be used to rotate the turbines without departing from the spirit and scope of the present invention. In accordance with an important aspect of the present invention, it will be noted that each of the four pump stages may be independently operated and controlled as to speed and output. It will be further apparent to those skilled in the art that the use of pump stages in pairs provides a redundant pump stage arrangement that allows either pump stage to continue to provide blood flow despite a failure of either pump stage.

In operation, the four pump stages of artificial heart 170 are driven in a similar manner to the above-described drive and control apparatus operative in combination with artificial heart 10. Accordingly, appropriate electrical signals are applied to drive coils 250, 251, 252 and 253 to induce rotation of magnetic rotors 260, 261, 262 and 263 which produces rotation of the rotatably supported turbines 210, 212, 211 and 213 along with their respective magnetic rotors 260, 261, 262 and 263. As is described in greater detail, it will be noted that the rotations of turbines 210 and 211 produce a straight through flow path between input 176 and output 177. This straight through flow path is enhanced by the venturi coupling between turbine receptacles 220 and 230 provided by surfaces 221, 222 and 231. The purpose of the venturi coupling is to increase the flow velocity between the pump turbines and further enhance the blood flow between input 176 and output 177. As a result of the straight-through blood flow thus produced, areas of stagnation and blood pooling are avoided.

In a similar fashion and for similar reasons, the blood flow from input 174 to output 175 between turbine receptacles 235 and 240 is similarly enhanced by the venturi coupling therebetween provided by surfaces 236, 237 and 241. Once again, a direct flow-through blood flow path between input 174 and output 175 is provided. This flow path is enhanced by the increased flow velocity created by the venturi coupling and avoids stagnation and blood pooling.

Figure 14:
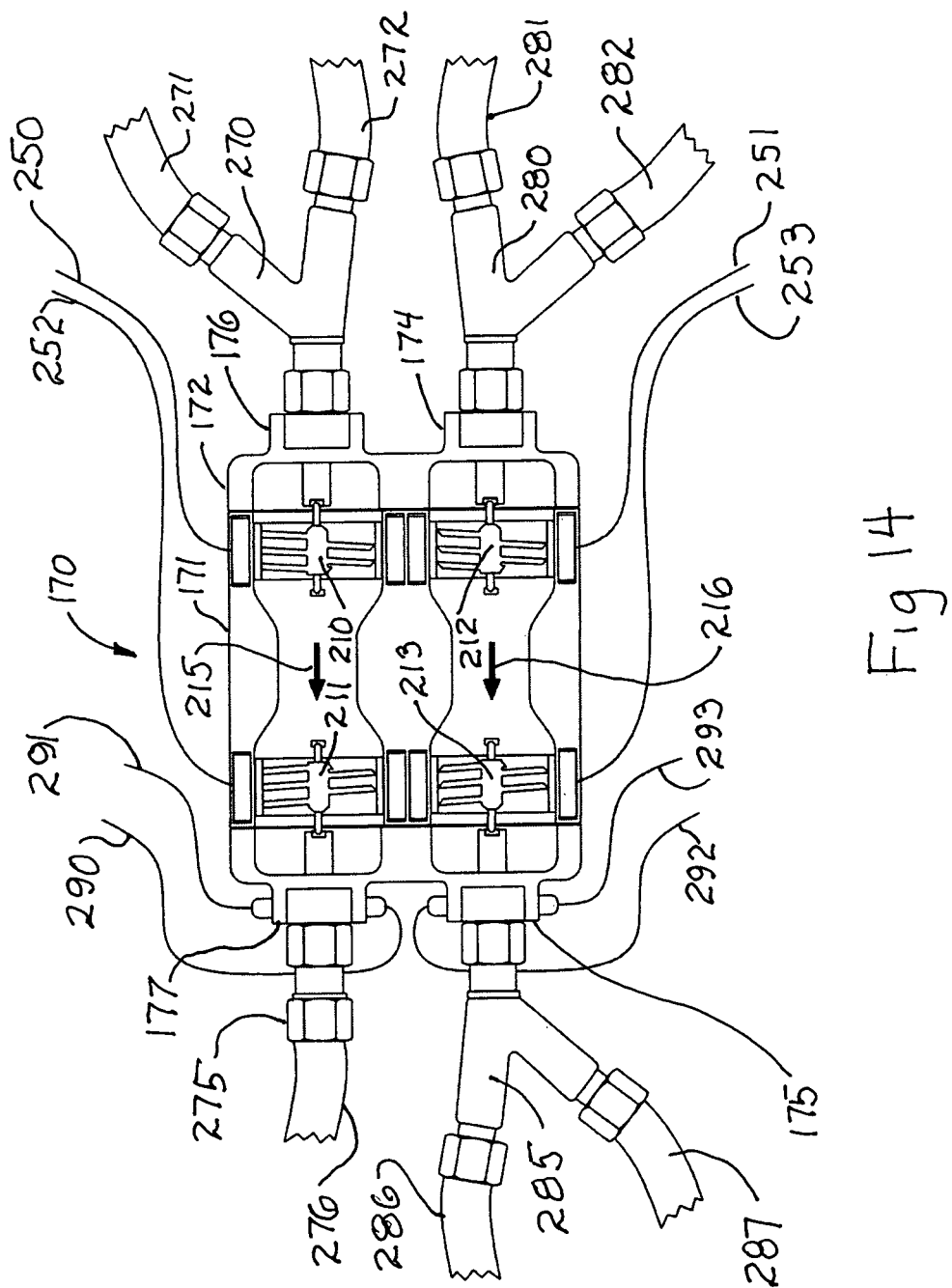
FIG. 14 sets forth a simplified section view of the embodiment of the present invention shown in FIG. 9 showing couplings to the recipient's circulatory and pulmonary systems.

FIG. 14 sets forth a section view of artificial heart 170 showing appropriate connections to the recipient's circulatory system. The blood flow connections are provided by medically approved tube elements and couplers.

More specifically, artificial heart 170 includes a center housing 171 defining a plurality of turbine receptacles 220, 230, 235 and 240. Receptacles 220 and 230 are aligned coaxially and define cylindrical receptacles. Turbine receptacles 220 and 230 are coupled by a venturi passage formed by a tapered portion 221, a center passage 222 and a tapered portion 231.

Turbine receptacles 235 and 240 are coaxially aligned and define cylindrical receptacles. Turbine receptacles 235 and 240 are coupled by a venturi portion formed by a tapered portion 236, a coupling portion 237 and a tapered portion 241.

Housing 171 further supports a generally cylindrical drive coil array 250 which encircles turbine receptacle 220. Drive coil assembly 250 provides a motor drive coil which is molded into housing 171. Drive coil 250 is coupled to a motor controller such as controller 140 set forth above in FIG. 8. Similarly, housing 171 supports a corresponding drive coil 252 which encircles turbine receptacle 230 and a drive coil 251 which encircles turbine receptacle 235 together with a drive coil 253 which encircles turbine receptacle 240. Drive coils 250, 251, 252 and 253 are substantially identical in fabrication.

Artificial heart 170 includes a turbine 210 and magnetic coupler 270 rotatably supported within turbine receptacle 220 by bearing supports 190 and 191. Artificial heart 170 further includes a turbine 212 and magnetic rotor 261 rotatably supported within turbine receptacle 235 by bearing supports 192 and 193. Artificial heart 170 further includes turbine 211 and magnetic rotor 262 rotatably supported within turbine receptacle 230 by bearing supports 194 and 195. Artificial heart 170 further includes turbine 213 and magnetic rotor 263 rotatably supported within turbine receptacle 240 by bearing supports 196 and 197.

Input 174 of pump 170 is coupled to a split coupler 280 which in turn is coupled to the recipient's superior vena cava by a tube 281 and is further coupled to the recipient's inferior vena cava by a tube 282. Similarly, output 175 is coupled to a split coupler 285 which is coupled to the recipient's pulmonary arteries by a pair of tubes 286 and 287. In addition, input 176 is coupled to a split coupler 270 which is coupled to the recipient's pulmonary veins by pair of tubes 271 and 272. Finally, output coupler 177 is coupled to a tube 276 by a coupler 275. Tube 276 is coupled to the recipient's aorta. Output coupler 177 further supports a pair of output transducers 290 and 291 while output 175 supports a pair of output transducers 292 and 293. Transducers 290, 291, 292 and 293 are coupled to the artificial heart controller in the manner set forth above in FIG. 7.

In operation, drive coils 250, 251, 252 and 253 are driven by the controller in the manner set forth above in FIG. 8 to produce rotations of turbines 210, 212, 211 and 213. As turbine 212 is rotated, blood is drawn through coupler 174 into pump 170 from the patient's superior and inferior vena cava through tubes 281 and 282. This blood flows through housing 171 in the direction indicated by arrow 216 and is further drawn by the rotation of turbine 213. The output from turbine 213 passes through output 175 and thereafter passes through split connector 285 and tubes 286 and 287 to the recipient's lungs. The rotation of turbine 210 draws blood from the patient's lungs through tubes 271 and 272 and split coupler 270 to input 176. Blood flows through turbine 210 in the direction indicated by arrow 215 and is further pumped by the rotation of turbine 211. The output of turbine 211 passes outwardly through output 177 and coupler 275 to be carried by tube 276 to the recipient's aorta for distribution throughout the recipient's circulatory system.

Thus as drive coils 251 and 253 are energized by the system controller, the rotation of turbines 212 and 213 provides a continuous straight through flow of blood from input 174 to output 175. This continuous straight through blood flow is in accordance with an important advantage of the present invention artificial heart in that the entire passage through both turbines 212 and 213 as well as the venturi coupled therebetween is a straight through continuous flow without areas of pooling or stagnation being created. Additionally, the series coupling of the pump segments provided by turbines 212 and 213 provide a redundancy which greatly increases the safety factor of the present invention artificial heart. Essentially, the failure of the drive apparatus operative upon either turbine 212 or turbine 213 does not interrupt blood flow in the direction indicated by arrow 216. In other words, should turbine 212 for some reason cease to rotate, the pumping action of turbine 213 continues and blood flows through turbine 212 virtually unobstructed in the direction indicated by arrow 216 continuing the vital blood flow from input 174 to output 175.

In a similar manner, the straight through construction of the pump segment provided by turbines 210 and 211 operates to maintain a blood flow in the direction indicated by arrow 215 from input 176 to output 177 notwithstanding a failure or other interruption of the rotation of either turbine 210 or 211. That is to say if turbine 210 ceases for whatever reason to rotate the pumping action provided by the rotation of turbine 211 continues to maintain blood flow in the direction indicated by arrow 215. Conversely, should turbine 211 for some reason cease rotation, the rotation of turbine 210 continues to provide blood flow in the direction indicated by arrow 215. It will be apparent to those skilled in the art that the combination of straight through blood flow and redundancy of pump turbine segments provides a substantial protection and safety factor for the present invention artificial heart.

Sensors 290 and 291 monitor the output pressure at output 177. Similarly, transducers 292 and 293 monitor the output pressure at output 175. In response to variations of sensed pressure at either of outputs 175 or 177, the system controller (seen in FIG. 8) is able to adjust the operating turbine segments of the artificial heart to compensate for any failures within the quartet of turbines. In addition, it will be apparent to those skilled in the art that the drive signals applied to drive coils 250 through 253 may be modulated or varied to provide a pulsitile output pressure from either or both of outputs 175 and 177. This pulsitile character imparts a more natural blood flow pattern for the recipient and may prove to be advantageous to the recipient.

What has been shown is a dual-stage redundant-turbine artificial heart which provides an implantable housing supporting a redundant set of servo driven turbine impeller pump portions to provide blood circulation within a host patient. Extreme reliability is provided by substantial redundancy beginning with redundant servo drive apparatus and extending to redundant turbine pump segments which are operated under the control of redundant microcontrollers. Each microcontroller is independently powered and driven by a battery unit and is configured to maintain operation in the event of failure within a servo drive or battery unit. Further redundancy is provided in that each microcontroller is configured to assume operation and control of artificial heart 10 should a microcontroller fail. In this manner, maximum redundancy provides corresponding maximum reliability for the inventive artificial heart apparatus.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. An artificial heart comprising:
a housing having a first input, a first output, a second input and a second output;
a first turbine pump operative to flow blood from said first input to said first output;
a second turbine pump operative to flow blood from said first input to said first output;
a third turbine pump operative to flow blood from said second input to said second output; and
a fourth turbine pump operative to flow blood from said second input to said second output.

2. The artificial heart set forth in claim 1 wherein said first and said second turbine pumps are arranged in parallel blood flow and said third and said fourth turbine pumps are arranged in parallel blood flow.

3. The artificial heart set forth in claim 1 wherein said first and said second turbine pumps are arranged in series blood flow and said third and said fourth turbine pumps are arranged in series blood flow.

4. The artificial heart set forth in claim 3 wherein said housing defines a plurality of turbine receptacles and wherein said first, second, third and fourth turbine pumps each include:
a respective turbine receptacle:
a turbine rotatably supported within said turbine receptacle:
a magnetic rotor rotatable with and supported by said turbine and
a drive coil supported within said housing and encircling said turbine receptacle and said turbine and said magnetic rotor.

5. The artificial heart set forth in claim 4 wherein said housing is
molded and wherein said drive coils are molded into said housing.

6. The artificial heart set forth in claim 5 wherein said turbines each include:
a turbine shaft having bearings at opposed ends thereof; and
a helical turbine blade supported upon and extending from said turbine shaft defining an outer edge.

7. The artificial heart set forth in claim 6 wherein each of said magnetic rotors are cylindrical and define a respective interior rotor surface and wherein each said outer edges of said each turbine are joined to a respective interior rotor surface to join said magnetic rotor to said turbine blades forming a single rotating unit.

8. An artificial heart comprising:
a housing having a first input, a first input turbine receptacle, a first output turbine receptacle, a first output and a first coupling passage between said first input turbine receptacle and said first output turbine receptacle, said first input, said first input turbine receptacle, said first output turbine receptacle, said first output and said first coupling passage being coaxial and said housing further having a second input, a second input turbine receptacle, a second output turbine receptacle, a second output and a second coupling passage between said second input turbine receptacle and said second output turbine receptacle, said second input, said second input turbine receptacle, said second output turbine receptacle, said second output and said second coupling passage being coaxial;
a first turbine pump supported within said first input turbine receptacle operative to flow blood from said first input through said first coupling passage to said first output turbine receptacle;

a second turbine pump supported within said first output turbine receptacle operative to flow blood from said first coupling passage to said first output;

a third turbine pump supported within said second input turbine receptacle operative to flow blood from said second input through said second coupling passage to said second output turbine receptacle; and a fourth turbine pump supported within said second output turbine receptacle operative to flow blood from said second coupling passage to said second coupling passage to said second output.

9. The artificial heart set forth in claim 8 wherein said first, second, third and fourth turbine pumps supported within a respective turbine receptacle each include:

a turbine rotatably supported within its respective turbine receptacle:

a magnetic rotor rotatable with and supported by said turbine and a drive coil supported within said housing and encircling said respective turbine receptacle and said turbine and said magnetic rotor.

10. The artificial heart set forth in claim 9 wherein said housing is molded and wherein
said drive coils are molded into said housing.

11. The artificial heart set forth in claim 10 wherein said turbines each include:

a turbine shaft having bearings at opposed ends thereof; and a helical turbine blade supported upon and extending from said turbine shaft defining an outer edge.

12. The artificial heart set forth in claim 11 wherein each of said magnetic rotors are cylindrical and define a respective interior rotor surface and wherein each said outer edges of said each turbine are joined to a respective interior rotor surface to join said magnetic rotor to said turbine blades forming a single rotating unit.

* * * * *